United States Patent
Leufkens et al.

(10) Patent No.: US 10,722,496 B2
(45) Date of Patent: *Jul. 28, 2020

(54) 2-IMINOBIOTIN FOR USE IN THE TREATMENT OF BRAIN CELL INJURY

(71) Applicant: Neurophyxia B.V., 's-Hertogenbosch (NL)

(72) Inventors: Paul Willem Theresia Josef Leufkens, 's-Hertogenbosch (NL); Cacha Marie Petronelle Catherine Dorothee Peeters, 's-Hertogenbosch (NL); Huibert Alexander Tjabbes, 's-Hertogenbosch (NL)

(73) Assignee: Neurophyxia B.V., 's-Hertogenbosch (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,226

(22) Filed: Jan. 3, 2020

(65) Prior Publication Data

US 2020/0147049 A1 May 14, 2020

Related U.S. Application Data

(63) Continuation of application No. 16/060,005, filed as application No. PCT/NL2016/050880 on Dec. 16, 2016, now Pat. No. 10,525,039.

(30) Foreign Application Priority Data

Dec. 16, 2015 (EP) .................................... 15200492

(51) Int. Cl.
*A61K 31/4164* (2006.01)
*A61K 31/4188* (2006.01)
*A61K 45/06* (2006.01)
*A61P 25/00* (2006.01)
*A61K 9/00* (2006.01)
*G01N 33/68* (2006.01)

(52) U.S. Cl.
CPC ........ *A61K 31/4188* (2013.01); *A61K 9/0019* (2013.01); *A61K 45/06* (2013.01); *A61P 25/00* (2018.01); *G01N 33/6893* (2013.01)

(58) Field of Classification Search
CPC ................................................. A61K 31/4164
USPC ......................................................... 514/402
See application file for complete search history.

(56) References Cited

U.S. PATENT DOCUMENTS

| 6,894,069 | B2 | 5/2005 | Peetres et al. |
| 7,087,633 | B2 | 8/2006 | Peeters et al. |
| 7,319,090 | B2 | 1/2008 | Katz |
| 9,023,878 | B2 | 5/2015 | Leufkens |
| 9,616,135 | B2 | 4/2017 | Leufkens |
| 10,525,039 | B2 * | 1/2020 | Leufkens ........... G01N 33/6893 |
| 2004/0002530 | A1 | 1/2004 | Peeters et al. |
| 2009/0197966 | A1 | 8/2009 | Weber et al. |
| 2013/0143936 | A1 | 6/2013 | Leufkens |
| 2015/0238513 | A1 | 8/2015 | Drew et al. |

FOREIGN PATENT DOCUMENTS

| WO | 00/42849 A1 | 7/2000 |
| WO | 01/74351 A1 | 10/2001 |
| WO | 2011/149349 A1 | 12/2011 |
| WO | 2013/182862 A1 | 12/2013 |
| WO | 2017/105237 A1 | 6/2017 |

OTHER PUBLICATIONS

Author unknown, TIBOHCA: Safety, tolerability and pharmacokinetics of 2-iminobiot in (2-IB) after OHCA (TIBOHCA), Jun. 1, 2016, https://clinicaltrials.gov/ct2/show/NCT028363409term iminobiotin+brain&rank=1, retrieved on Mar. 20, 2017.
Debillon et al., Whole-body cooling after perinatal asphyxia: a pilot study in term neonates, Development medicine and child neurology, 2003, pp. 17-23, vol. 45.
Groenendaal et al., Early Human Development, 2009, vol. 85, pp. 73-76 (published Online Jan. 6, 2009).
Loftsson, Cyclodextrins, 36 pages, Jornal of Pharmaceutical Science, May 5, 2004, vol. 93, No. 5.
PCT International Search Report, PCT/NL2016/050880, dated Mar. 4, 2017.
PCT International Written Opinion, PCT/NL2016/050880, dated Mar. 4, 2017.
Perrone et al., 2-Iminobiotin for the treatment of perinatal asphyxia, Expert Opinion on Orphan Drugs, Oct. 21, 2013, pp. 935-945, vol. 1, No. 11.
Van Dijk, et al., The effect of administration of 2-iminobiotin at birth on growth rates, morbidity and mortality in piglets under farm conditions, Livestock Science, 2008, pp. 129-136, vol. 115, Science Direct, Elsevier.
Zitta Karina et al: "Insights into the neuroprotective mechanisms of 2-iminobiotin employing an in-vitro model of hypoxic-ischemic cell injury", European Journal of Pharmacology, vol. 792, Oct. 23, 2016 (Oct. 23, 2016), pp. 63-69.

* cited by examiner

*Primary Examiner* — Raymond J Henley, III
(74) *Attorney, Agent, or Firm* — TraskBritt

(57) ABSTRACT

The present disclosure relates to the use of 2-iminobiotin for treating brain cell injury, in particular in adults. The treatment may be used for the treatment of cerebral hypoxia-ischemia and/or reperfusion injury, including one or more symptoms thereof. Provided are methods of treatment comprising administering a therapeutically effective dose of 2-iminobiotin to an individual in need thereof.

20 Claims, 19 Drawing Sheets

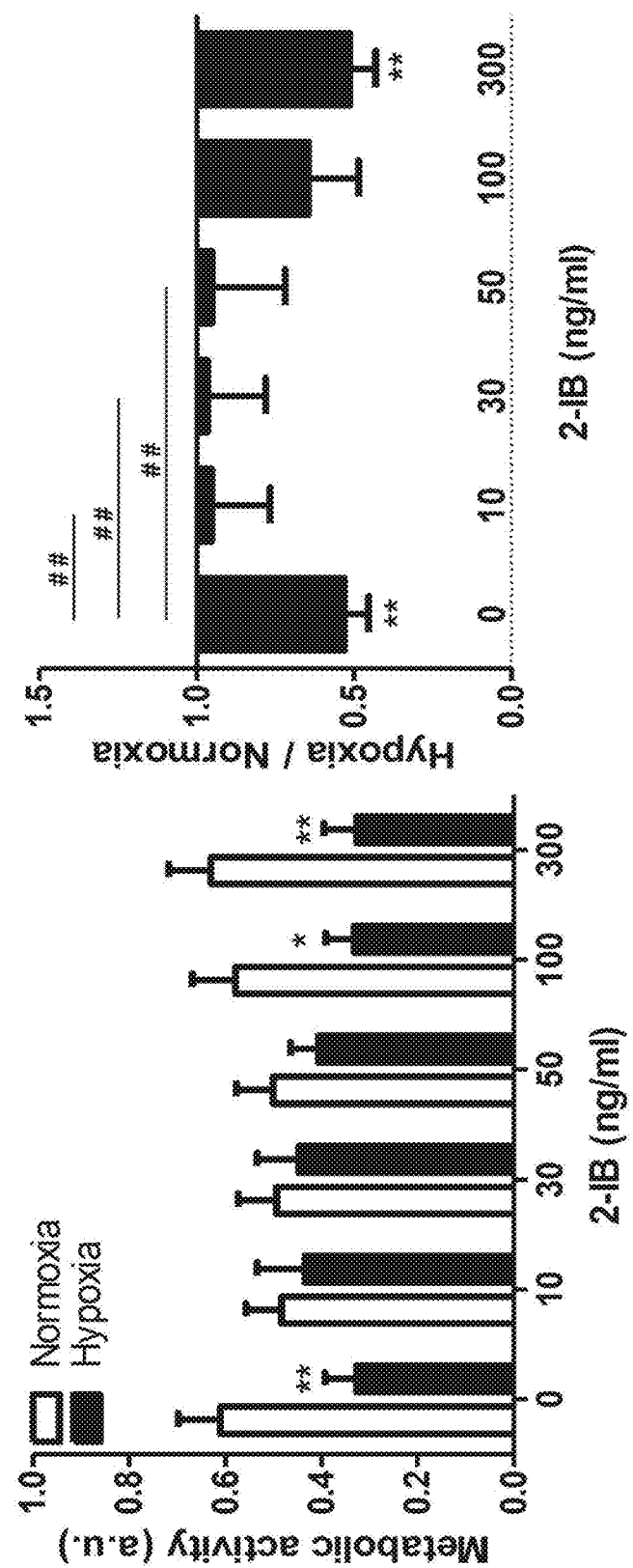

2-IMINOBIOTIN FOR USE IN THE TREATMENT OF BRAIN CELL INJURY

CROSS-REFERENCE TO RELATED APPLICATIONS

This application is a continuation of U.S. patent application Ser. No. 16/060,005, filed Jun. 6, 2018, which has issued as U.S. Pat. No. 10,525,039 on Jan. 6, 2020, which is a national phase entry under 35 U.S.C. § 371 of International Patent Application PCT/NL2016/050880, filed Dec. 16, 2016, designating the United States of America and published in English as International Patent Publication WO 2017/105237 A1 on Jun. 22, 2017, which claims the benefit under Article 8 of the Patent Cooperation Treaty to European Patent Application Serial No. 15200492.5, filed Dec. 16, 2015.

TECHNICAL FIELD

The application relates to the use of 2-iminobiotin for treating brain cell injury, particularly in adults. The treatment may be used for the treatment of cerebral hypoxia-ischemia and/or reperfusion injury, including one or more symptoms thereof. Provided are methods of treatment comprising administering a therapeutically effective dose of 2-iminobiotin to an individual in need thereof.

BACKGROUND

Heart disease, including cardiac arrest, is the most frequently occurring cause of death in the USA (Heron, NVSR, 2015). From the cases that experienced a witnessed out of hospital cardiac arrest (OHCA), overall survival was 11.7% (Ewy et al., 2015). These outcomes, however, are dependent on multiple patient related and non-patient related factors (Shah et al., 2014; Mosier et al., 2010; Hasan et al., 2014; Mauri et al., 2015; Warren et al., 2015; Iqbal et al., 2015).

Predicting patients' functional outcome in early stages after OHCA is difficult. Often the Cerebral Performance Category (CPC) at discharge is used as a quick screening instrument/tool. An overall good neurological outcome, defined as a CPC score of 1 or 2 at discharge, is reported in 6.5% of patients after witnessed OHCA (Ewy et al., 2015). However, the CPC score alone is not sufficient to assess patients' functioning (Wallin et al., 2014). In survivors of OHCA between 30% and 50% experience cognitive deficits up to several years post-discharge (Green et al., 2015). Also cognitive impairment, mainly memory problems, is present in 29% of OHCA survivors with initial good neurological outcome at hospital discharge (Buanes et al., 2015). Especially spatial memory is affected due to ischemia-induced neuronal damage in the hippocampus.

To improve survival and to decrease the degree of neurological impairment, the implementation of therapeutic hypothermia after OHCA has been investigated. No difference in cognitive function was demonstrated between patients who received hypothermia (32° C.-34° C.) and controlled normothermia (36° C.) (Lilja et al., 2015). For that reason new strategies are being explored to reduce the consequences on cognition after cerebral hypoxia-ischemia, such as after OHCA and other diseases in which ischemia and reperfusion injury takes place.

BRIEF SUMMARY

The disclosure provides methods for the treatment of brain cell injury in an individual, comprising providing an individual in need thereof with a therapeutically effective amount of 2-iminobiotin (2-IB). The disclosure provides 2-IB for use in the preparation of a medicament for the treatment of brain cell injury. The disclosure provides 2-IB for use in the treatment of brain cell injury in an individual. The methods and uses are for treatment in an individual that is not a neonate, i.e., is older than a neonate.

Preferably, 0.05 to 10 mg/kg/day of 2-IB is administered to the individual. Preferably, 0.2 to 10 mg/kg/day of 2-IB, more preferably, 0.2 to 5 mg/kg/day of 2-iminobiotin, is administered to the individual.

Preferably, treatment with 2-IB is combined with hypothermia. Preferably, treatment is combined with hypothermia and 0.01 to 10 mg/kg/day of 2-IB is administered to the individual.

Preferably, 0.1 to 10 mg/kg/day of 2-iminobiotin is administered to the individual, wherein the 2-iminobiotin is administered every four to six hours per day, preferably every four hours. Preferably, the treatment is combined with 36° C. targeted temperature management.

Preferably, between 2-20, more preferably between 3-13 mg of 2-IB is administered per dose.

In preferred embodiments, 0.01 to 1.5 mg/kg/day of 2-iminobiotin is administered to the individual, wherein the 2-iminobiotin is administered every four to six hours, preferably every six hours, wherein treatment is combined with hypothermia. Preferably, wherein 0.03 to 1 mg/kg/day of 2-iminobiotin is administered, preferably, wherein 0.03 to 0.4 mg/kg/day of 2-iminobiotin is administered when the treatment is combined with hypothermia. Preferably, wherein between 0.7-8 mg, more preferably between 1-5 mg of 2-IB is administered per dose.

Preferably, 2-iminobiotin is provided for use in the treatment of brain cell injury in an individual, wherein between 18-78 mg/day of 2-iminobiotin is administered, where the 2-iminobiotin is provided in at least three doses per day, preferably in at least six doses per day, and wherein the individual is not a neonate. Preferably, the 2-IB is provided continuously, every 2-10 hours, every 3-8 hours, most preferably every 4-6 hours. Preferably, the treatment is combined with 36° C. targeted temperature management.

2 Preferably, -iminobiotin for use in the treatment of brain cell injury in an individual, wherein between 4-20 mg/day of 2-iminobiotin is administered, where the 2-iminobiotin is provided in at least three doses per day, preferably in at least four doses per day, wherein treatment is combined with hypothermia. Preferably, the 2-IB is provided continuously, every 2-10 hours, every 3-8 hours, most preferably every 6-8 hours, in particular every 6 hours.

In preferred embodiments, the 2-iminobiotin dose is adjusted based on the individual's renal function. Preferably, the 2-iminobiotin dose is adjusted based on the individual's serum creatinine level. Preferably, the 2-iminobiotin dose is adjusted based on the individual's estimated glomerular filtration rate (eGFR).

Preferably, 2-iminobiotin is administered such that the area under the plasma concentration time curve at 4 hours is between 100 ng·h/mL to 2000 ng·h/mL, more preferably between 300 ng·h/mL to 1300 ng·h/mL.

Preferably, the brain cell injury is cerebral hypoxia-ischemia and/or reperfusion injury. Preferably, the brain cell injury is reperfusion following cerebral hypoxia-ischemia. Preferably, the brain cell injury is associated with cardiac arrest.

Preferably, individual is a human of at least one year of age. Preferably, human is of at least two years of age.

Preferably, the 2-iminobiotin is administered parenterally or intravenously.

Preferably, wherein the 2-iminobiotin is administered for at least 24 hours. Preferably, at least four, more preferably at least six, doses of 2-iminobiotin are administered.

Preferably, the 2-iminobiotin is administered prophylactically, i.e., before brain cell injury (such as cerebral hypoxia-ischemia and/or reperfusion injury) has occurred.

In some embodiments, provided is a method of determining a dosage of 2-iminobiotin for treating brain cell injury in an individual, the method comprising determining the serum creatinine concentration or estimated glomerular filtration rate (eGFR) in the individual and adjusting the 2-iminobiotin dosage based on the serum creatinine level or eGFR.

BRIEF DESCRIPTION OF THE DRAWINGS

FIGS. 2A-2D: Effects of 2-IB on hypoxia-induced cell damage and metabolic activity. 2-IB attenuates hypoxia-induced cell damage (FIGS. 2A and 2B) and increases metabolic activity under hypoxic conditions (FIGS. 2C and 2D), showing a U-shaped dose response curve. Columns display the mean; bars denote SD. FIGS. 2A and 2C: *, $P<0.05$; , $P<0.01$; *, $P<0.001$ all vs. the respective normoxia control. FIGS. 2B and 2D: *, $P<0.05$ vs. 1; **, $P<0.01$ vs. 1; #, $P<0.05$; ##, $P<0.01$.

FIG. 3A: *, $P<0.05$; **, $P<0.01$; all vs. the respective normoxia control. FIG. 3B: *, $P<0.05$ vs. 1; **, $P<0.01$ vs. 1; #, $P<0.05$.

FIG. 7A: , $P<0.01$; *, $P<0.001$ all vs. the respective normoxia control. FIG. 7B: *, $P<0.05$ vs. 1; , $P<0.01$ vs. 1; *, $P<0.001$ vs 1.

FIG. 8A: $P<0.01$; ***, $P<0.001$ all vs. the respective normoxia control. FIG. 8B: *, $P<0.05$ vs. 1; , $P<0.01$ vs. 1; *, $P<0.001$ vs 1.

DETAILED DESCRIPTION

Figure 1:
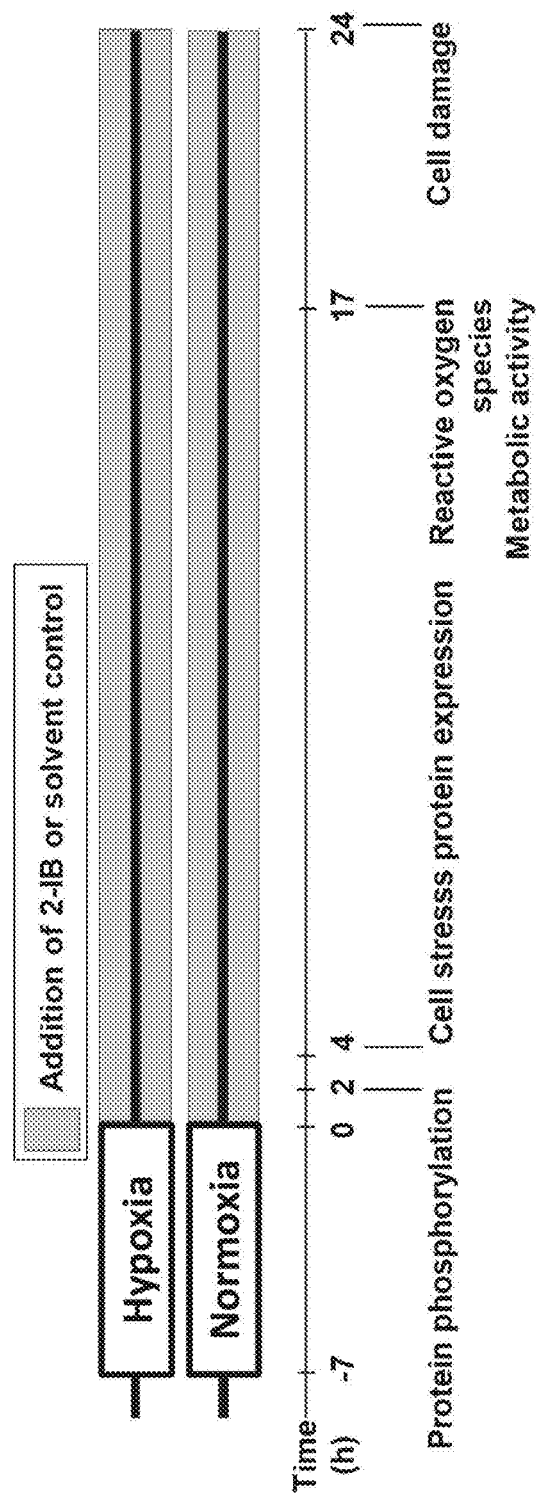
FIG. 1: Experimental setup.

2-Iminobiotin (2-IB), a biotin analogue, reduces the amount of neurological damage in a piglet model of perinatal global hypoxia-ischemia (HI) (Peeters-Scholte et al., 2002). 2-IB is currently in clinical Phase 2 trials for this indication in neonates. Although the neonatal brain is not just a small adult brain and the underlying (patho)physiological pathways vastly differ, the present disclosure surprisingly demonstrates that 2-IB is an effective treatment for hypoxia-ischemia-induced neuronal damage in adults as well.

Provided are methods of treating brain cell injury in adults, adolescents, and juveniles. Although 2-IB has been used in neonates, there are important differences between the neonate and an individual older and more developed than a neonate, such as an adult and older child. A few of the many differences are summarized below.

Neonates differ from older animals in maturation of development of the brain and in capacity of anti-oxidant systems (Ferriero et al., 2010 and Ben-ari et al., 2012). They have distinct ways for inducing and regulating apoptosis and they differ in metabolism (Cella et al., 2011). There is also a difference between the immature and the mature brain in sensitivity to processes involved in secondary cell death (Vannucci et al., 2004). Furthermore, there is a developmental switch between excitatory and inhibitory GABA(A) receptor-mediated responses during brain development (W. Kilb, 2012) and the myelination process of the developing brain is still ongoing during the first 1.5 years (R. L. Haynes, et al., 2005).

Finally, the blood brain barrier of the neonate is not yet mature and functions differently from the mature blood brain barrier, specifically with regard to the permeability for small molecules. Saunders et al. reports that there is a decline in permeability to low molecular weight lipid-insoluble compounds during brain development. (Saunders et al., 2000). More recently it has been shown that the BBB of a neonate reacts differently on hypoxic-ischemic injury compared to that of an adult (D. F. Lopez et al., 2012). Other differences in the BBB between newborns and older individuals are described in Saunders et al., 2012. In conclusion, it is clear that it is not possible to extrapolate therapeutic dosages of a drug from a neonate to an adult, as is the case with 2-IB.

In addition to the many differences between the neonatal brain and the adult brain, neonates also have differences in metabolism in comparison to adults. Important alterations in renal clearance and hepatic metabolism occur in perinatal life and the pharmacology of many drugs differs substantially in the newborn compared to the adult (Mulberg et al., 2009).

In one aspect of the disclosure, methods are provided for the treatment of brain cell injury in an individual comprising administering to an individual in need thereof a therapeutically effective amount of 2-IB.

Preferably, 2-IB is administered to an individual such that the area under the plasma concentration time curve after the first dose (from 0 to 4 hours, AUC 0-4 hours) for 2-IB is at least 100 ng·h/mL, more preferably at least 3090 ng·h/mL. Preferably, the AUC 0-4 hours is at least 356 ng·h/mL. In some embodiments, the AUC 0-4 hours is between 100 ng·h/mL to 2000 ng·h/mL, between 100 ng·h/mL to 1300 ng·h/mL, between 300 ng·h/mL to 2000 ng·h/mL, or between 300 ng·h/mL to 1300 ng·h/mL. Preferably, the AUC 0-4 hours is less than 2000 ng·h/mL, more preferably, less than 1300 ng·h/mL. As explained in the examples herein, the disclosure provides that the minimum target exposure for treatment is around 356 ng·h/mL (plasma concentration) and that levels up to an including 1068 ng·h/mL (plasma concentration) are also effective. The disclosure provides a number of dosage regimes that provide the appropriate 2-IB exposure levels.

In preferred embodiments, the methods comprise administering 0.01 to 10 mg/kg/day of 2-IB to the individual. Preferably, 0.05 to 10 mg/kg/day of 2-IB is administered, more preferably, 0.2 to 10 mg/kg/day. Other preferred dosages of 2-IB include 0.05 to 5 mg/kg/day, 0.1 to 5 mg/kg/day, and 0.2 to 5 mg/kg/day. Other preferred dosages of 2-IB include 0.05 to 3 mg/kg/day, 0.1 to 3 mg/kg/day, and 0.2 to 3 mg/kg/day. Other preferred dosages of 2-IB include 0.05 to 1.5 mg/kg/day, 0.1 to 1.5 mg/kg/day, and 0.2 to 1.5 mg/kg/day. Other preferred dosages of 2-IB include 0.05 to 1 mg/kg/day, 0.1 to 1 mg/kg/day, and 0.2 to 1 mg/kg/day. Other preferred dosages of 2-IB include 0.05 to 0.5 mg/kg/day, 0.1 to 0.5 mg/kg/day, and 0.2 to 0.5 mg/kg/day. Most preferred is a dosage of 0.1 to 10 mg/kg/day. These amounts refer to the active component and do not include carrier or adjuvant materials such as carbohydrates, lipids or proteins or the like. As discussed further herein, 2-IB is preferably administered several times per day. In a non-limiting exemplary embodiment, a 0.1 to 10 mg/kg/day dosage may be provided as six doses of 0.016-1.6 mg of 2-IB every four hours.

The 2-IB treatment described herein may involve a single administration, but usually—and preferably—involves multiple administrations over several hours or days. The daily dosage of 2-IB referred to herein may be administered as a single dose or as multiple doses per day, or essentially continuously over a certain period of time, e.g., by continuous infusion.

Figure 16A:
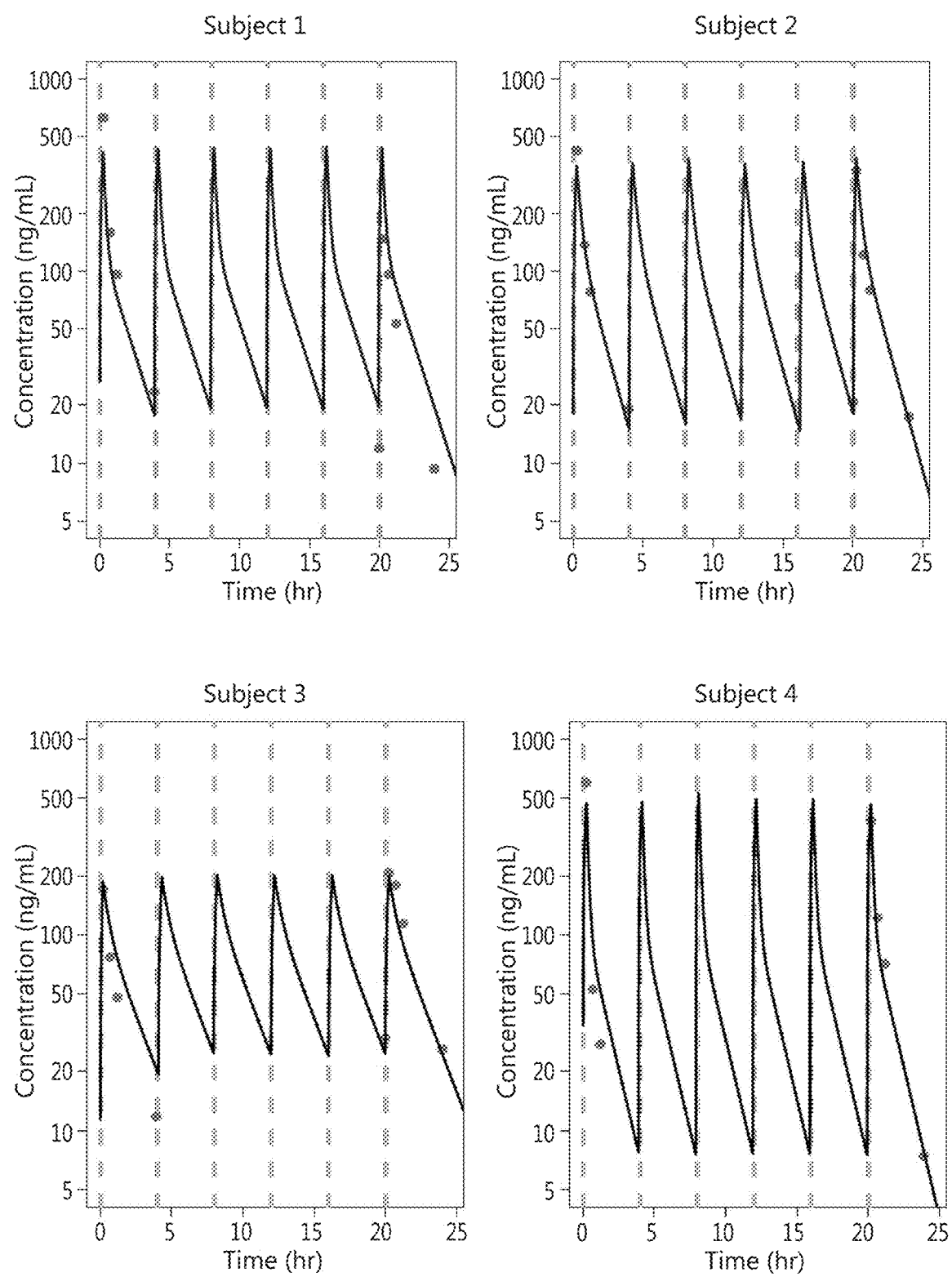
FIGS. 16A and 16B: Fitted serum 2-IB concentrations with IV-infusion every four hours. The dots on the graph represent measured values, which have been extrapolated.
Figure 16B:
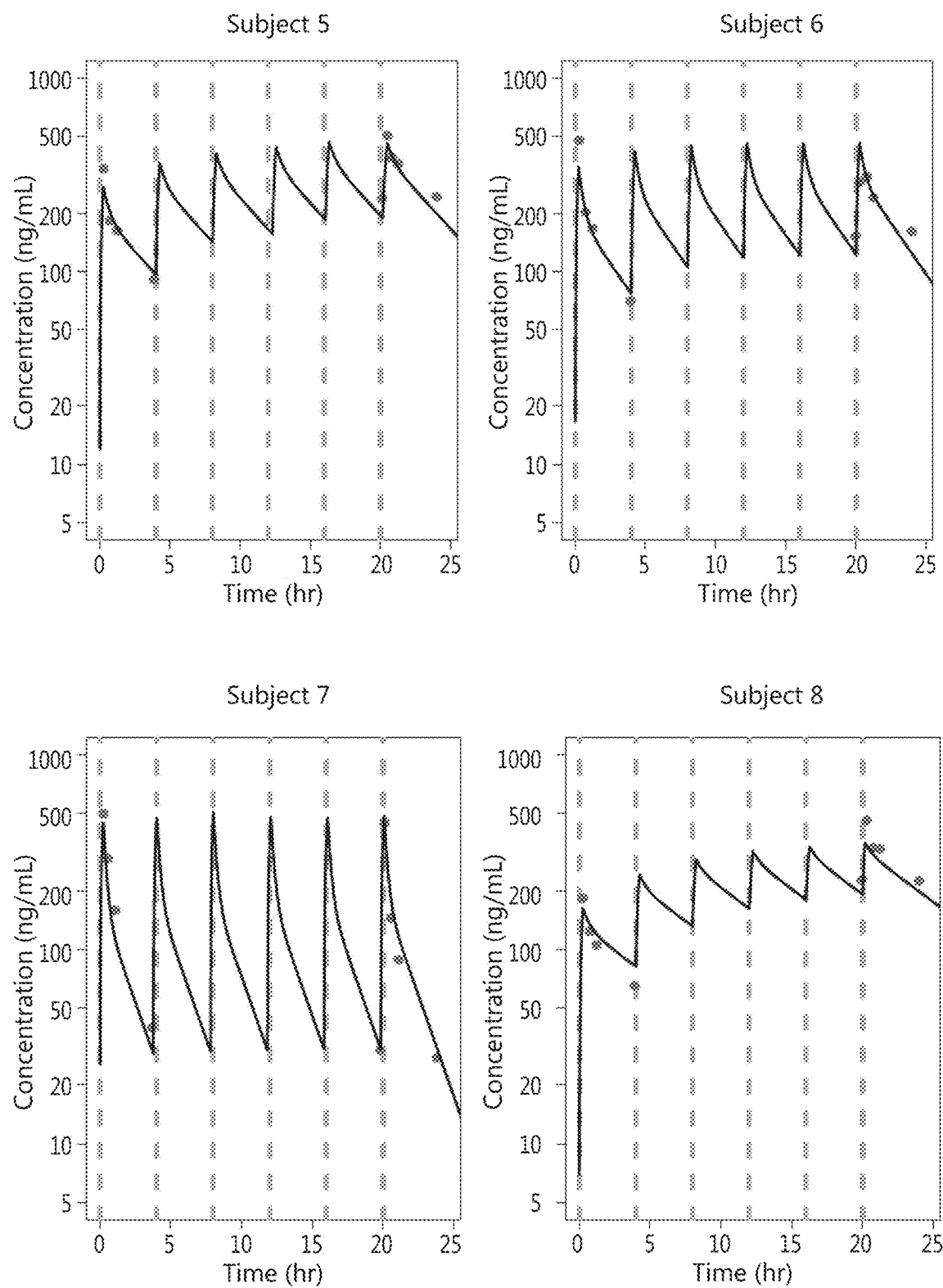
Figure 17:
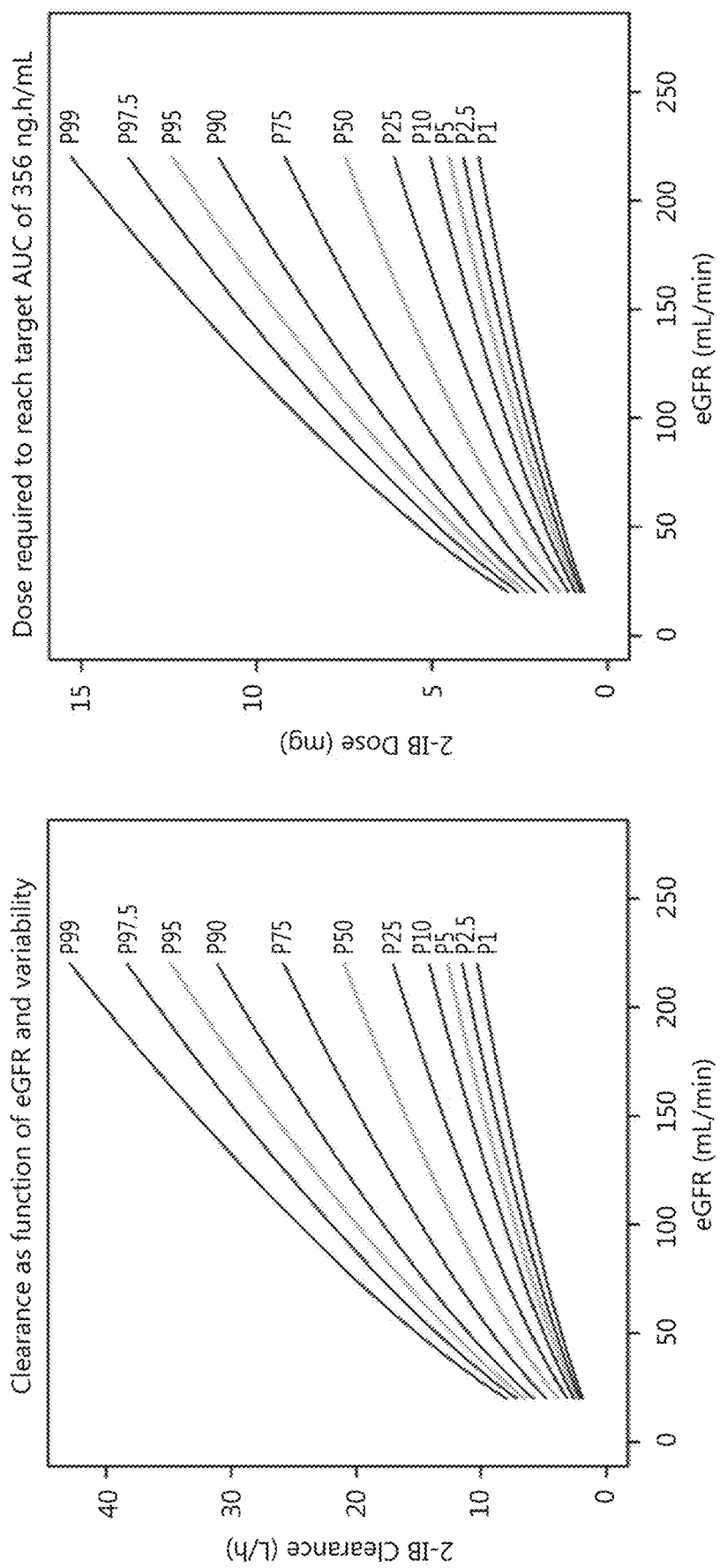
FIG. 17: Clearance and the dose required to reach the target vary as a function of eGFR.
Figure 18:
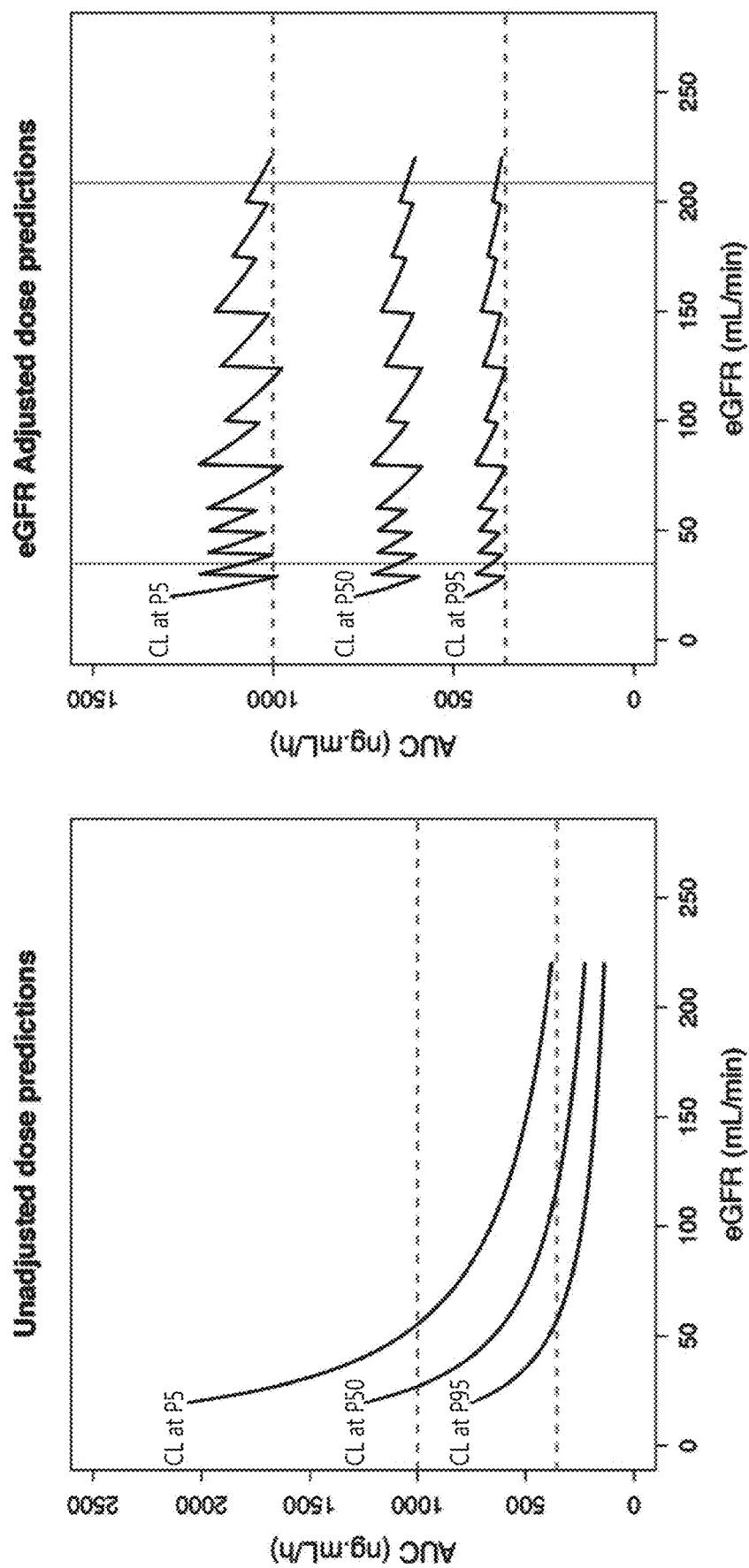
FIG. 18: Unadjusted and eGFR adjusted dose predictions. The dotted lines indicate the upper and lower target exposure of 356 ng·mL/h and 1068 ng·mL/h.

Preferably, the 2-IB is administered every 4 or 6 hours, i.e., the 2-IB is administered 4-6 times per day. In some embodiments, the 2-IB is administered every 3-8 hours, i.e., 3-8 times per day. When combined with hypothermia, the 2-IB is preferably administered every 6 hours. It is clear to a skilled person that the dosage administered can be administered over an extended period. Preferably, the 2-IB is administered as a slow bolus IV infusion. Preferably, the 2-IB is administered as a 15 minute IV infusion. As an exemplary embodiment, 6 mg of 2-IB is administered as a 15 minute IV infusion six times per day (i.e., at around every 4 hours). Although not wishing to be bound by theory, FIGS. 16A and 16B demonstrate that administering 2-IB at low doses several times per day provides the target minimum exposure level of 2-IB.

As described in Example 5B, the disclosure provides that body weight has minimal effect on 2-IB exposure. In preferred embodiments, doses not influenced by weight may be provided. Preferably, the individuals treated with the doses independent of weight disclosed herein range from 20 to 200 kg, more preferably ranging from 30 kg to 180 kg.

Preferably, the total daily dose is between 6-120, more preferably between 12 to 120 mg, most preferably between 18-78 mg. Preferably, the daily dose is administered as at least three doses, i.e., at at least three separate time points; preferably between 3-10 doses. It is clear to a skilled person, that administration of at three doses or at least three separate time points encompasses continuous infusion. Preferably, the daily dose is administered as at least four doses, i.e., at at least four separate time points. Most preferably, the daily dose is administered as at least six doses, i.e., at at least six separate time points. It is clear to a skilled person that the time between each dose (or time point) should be essentially the same. Preferably, 2-IB is administered at a dosage of between 2-39 mg, between 2-20 mg, between 3-39 mg, more preferably between 3-13 mg, most preferably between 3-12.75 mg, preferably administered six times per day.

Preferably, 2-IB is administered as a unit dosage of 3 mg, 4 mg, 5 mg, 6 mg, 7 mg, 8 mg, 9 mg, 10 mg, 11 mg, 12 mg, or 13 mg. In a non-limiting exemplary embodiment, an individual weighing 80 kg may receive six doses of 2-IB in a day, wherein each dosage comprises 3-13 mg. The individual would thus receive 0.04-0.16 mg/kg/dose and 0.23-0.94 mg/kg/day.

As described in Example 5B, the disclosure provides that 2-IB clearance is associated with renal function, in particular by the glomerular filtration rate (GFR). In preferred embodiments, the 2-IB dosage may be adjusted based on the individual's renal function or renal clearance. This may be expressed as the Glomerular filtration rate (GFR) and approximated by the Creatinine clearance rate, which can be calculated using serum Creatinine levels.

In preferred embodiments, the 2-IB dosage may be adjusted based on the individual's serum creatinine level. Creatinine is a byproduct of muscle metabolism and typically remains in a steady state balanced by renal elimination. Serum creatinine levels can be determined by a number of known methods known to one of skill in the art and a number of point-of-care tests are also available, see, e.g., iSTAT Portable Clinical Analyzer (reviewed in Clin. Chim. Acta. 2012 Jan. 18; 413(1-2):88-92) and the CardioChek Silver PA Analyzer. Accordingly, the disclosure provides methods for determining a dosage of 2-iminobiotin for treating brain cell injury in an individual, the method comprising determining the serum creatinine in the individual and adjusting the 2-iminobiotin dosage based on the serum creatinine level.

Preferably, the 2-IB dosage is adjusted based on serum creatinine. SeCre adjusted doses are particularly useful for individual's having a high GFR. For these individuals, the dose of 2-IB can be increased in order to ensure that the target exposure is reached. An exemplary dosing scheme for males based on serum creatinine (SeCre) is as follows:

SeCre of less than 30 µM, 12-20 mg/dose, preferably 15-18.75 mg/dose.
SeCre of between 30 to 40 µM, 8-17 mg/dose, preferably 10-15 mg/dose.
SeCre of between 41 to 50 µM, 6-14 mg/dose, preferably 7.5-12 mg/dose.
SeCre of between 51 to 60 µM, 5-11 mg/dose, preferably 6-9.75 mg/dose.
SeCre of between 61 to 80 µM, 4-9 mg/dose, preferably 5-8.25 mg/dose.
SeCre of between 81 to 100 µM, 3-7 mg/dose, preferably 4-6 mg/dose.
SeCre of between 101 to 125 µM, 2-6 mg/dose, preferably 3-5.25 mg/dose.
SeCre of between 126 to 150 µM, 2-5 mg/dose, preferably 2.5-4.5 mg/dose.
SeCre of between 150 to 200 µM, 2-4 mg/dose, preferably 2-3.75 mg/dose.

Preferably, the 2-IB dosage is adjusted based on eGFR. eGFR is based on serum creatinine levels and takes into account both the age and sex of the individual. An exemplary formula for determining eGFR is as follows:

$$eGFR = 186 * SeCr^{-1.154} * Age^{-0.203} * 0.724^{SEX}$$

Sex: males=0; females=1.

eGFR adjusted doses are particularly useful for individual's having a high GFR. Accordingly, the disclosure provides methods for determining a dosage of 2-iminobiotin for treating brain cell injury in an individual, the method comprising determining the eGFR in the individual and adjusting the 2-iminobiotin dosage based on the eGFR. An exemplary dosing scheme based on eGFR is as follows, however a skilled person will recognize that the dosages may vary as much as 10 or 20% (±/−) as listed below.=

| eGFR (mL/minute) | | Preferred |
| --- | --- | --- |
| low | high | Dose (mg) |
| 20 | <30 | 3.00 |
| 30 | <40 | 3.75 |
| 40 | <50 | 4.50 |
| 50 | <60 | 6.00 |
| 80 | <100 | 7.50 |
| 100 | <125 | 8.25 |
| 125 | <150 | 9.75 |
| 150 | <175 | 11.25 |
| 175 | <200 | 12.00 |
| 200 | <220 | 12.75 |

As used herein, the terms "treatment," "treat," and "treating" refer to alleviating, delaying or preventing the onset of, or inhibiting or reducing the progress of brain cell injury, or one or more symptoms associated with brain cell injury. In particular, the brain cell injury is associated with hypoxia, ischemia, anoxia, neurodegeneration, CNS infections, or traumatic brain injury.

In preferred embodiments, the brain cell injury is cerebral hypoxia-ischemia. Ischemia is a deficiency of blood flow resulting in the loss of physiological homeostasis and may lead to ischemic infarction and eventually to cellular death via apoptosis. Hypoxia is reduced oxygen availability in tissue. Hypoxia may result from ischemic events. As used herein, "hypoxia" means a reduction in oxygen supply to tissues below physiological levels. As used herein, "normoxia" means a normal or physiological level of oxygen supply to bodily tissues. Hypoxia thus also comprises anoxia which is a complete tissue deprivation of oxygen supply.

Cerebral hypoxia-ischemia is hypoxia-ischemia of the brain tissues resulting in loss of brain cells. Unlike other tissue which can survive extended periods of hypoxia-ischemia, brain tissue is particularly sensitive to deprivation of oxygen or energy. Permanent damage to neurons can occur even during very brief periods of hypoxia-ischemia. Cerebral ischemia includes focal cerebral ischemia, which occurs, e.g., when a blood clot has occluded a cerebral vessel and is confined to a specific region of the brain, often caused by thrombosis or embolism, and global cerebral ischemia, which occurs, e.g., when blood flow to the entire brain is stopped or drastically reduced, and is commonly caused by cardiovascular disease, but also during, e.g., near-drowning and strangulation.

Cerebral ischemia and brain hypoxic injury may occur, e.g., under conditions of stroke, acute ischemic stroke, transient ischemic attack, acute hemorrhagic stroke, head trauma, brain hemorrhages, cardiac arrest, cerebral edema, hydrocephalus, asphyxia, vaso-occlusive conditions, (arterial and venous) embolism, thrombosis, thromboembolism, atherosclerosis, prolonged severe hypotension, drowning, strangulation, cardiac surgery complications or neurosurgery complications. Cerebral hypoxia-ischemia may also result from neurodegeneration, traumatic brain injury and CNS infections. Preferably, the methods described herein are for treating cardiac arrest.

In preferred embodiments, treatment with 2-IB prevents, reduces the severity of, or slows the onset of one or more symptoms of cerebral ischemia and/or brain hypoxic injury. Such symptoms include cognitive, sensory or motor problems, depending on the extent and regions of the brain which are damaged. These symptoms include paralysis or loss of muscle movement, difficulty walking, talking or swallowing (including dysarthria, dysphagia, and aphasia), and defects in working memory, attention, learning, calculation, visual perception, or executive function (i.e., decision making, organization, and problem solving).

In preferred embodiments, the brain injury is reperfusion injury. Reperfusion injury is the damage caused when blood supply returns to tissue after a period of ischemia or lack of oxygen (anoxia, hypoxia). Preferably, the reperfusion injury is the result of cerebral ischemia-hypoxia. The absence of oxygen and nutrients from blood creates a condition in which the restoration of circulation results in inflammation and oxidative damage through the induction of oxidative stress rather than restoration of normal function. Reperfusion can occur, for example, after resuscitation from cardiac arrest, drowning, strangulation or revascularization after myocardial infarction or cerebral ischemic stroke.

In some embodiments, methods are provided to treat reperfusion injury in an individual after the onset of cerebral hypoxia-ischemia in the individual. The methods may also be used to treat reperfusion injury in an individual at risk of cerebral hypoxia-ischemia, for example, in an individual undergoing cardiac or thoracic aortic surgery.

2-IB is preferably administered as soon as possible after injury or after an injury causing event. For example, an individual is preferably treated as soon as possible after going into cardiac arrest. Preferably, the injury causing event is reperfusion. In preferred embodiments, 2-IB is administered to an individual that has suffered cerebral hypoxia-ischemia. In preferred embodiments, 2-IB is administered to an individual after reperfusion has taken place, for example, following cerebral hypoxia-ischemia.

Preferably, the patient is treated within 24 hours from the injury or injury causing event. Treatment may be continued up to 24, 48 or 72 hours after cerebral hypoxia-ischemia or the injury causing event. Treatment may also be continued until the individual is judged no longer to be at risk, e.g., in the case of infections, treatment may continue for 24 hours after the individual is infection-free. In preferred embodiments, the individual is treated within 6 hours from reperfusion, e.g., 6 hours after resuscitation, more preferably within 4 hours from reperfusion, and even more preferably within 2 hours from reperfusion. In some embodiments, the individual is treated initially with hypothermia and is treated within 12, preferably within 8 hours from reperfusion.

As used herein, treatment also includes prophylactic treatment in order to prevent or minimize brain cell injury. For example, 2-IB may be administered prophylactically during or before cardiac or thoracic aortic surgery in the event that such procedures may lead to cerebral ischemia. In these embodiments, 2-IB may, e.g., be administered 6 hours prior to surgery with treatment continuing for 24 hours after surgery. In some embodiments, 2-IB may be administered 1-5 hours prior to surgery. In other embodiments, 2-IB, in particular 2-IB provided parenterally, may be administered immediately (e.g., within 10 minutes) before surgery. For individuals at risk of cerebral hypoxia-ischemia, long term treatment may be indicated, e.g., treatment for several weeks. Preferably, 2-IB is administered orally for long-term treatment.

As used herein, the term "individuals" refers to any mammal, such as humans, non-human primates, rodents, guinea pigs, rabbits, sheep, pigs, goats, cows, horses, dogs, and cats. Preferably, the individual is a human. The administration protocols described herein are for treating adult (fully-developed) as well as juvenile (developing) mammals. The individuals described herein do not encompass neonates. The duration of the state of neonaticity varies per animal species and is known to a skilled person. In mammals neonaticity lasts until about 4 weeks after birth. Preferably, the individuals referred to herein are at least 6 weeks old, more preferably, at least 6 months old. In preferred embodiments, the individual is a human that is at least one year old, more preferably at least two years old. In some embodiments the individual is a human who is at least three years old.

In a preferred embodiment, 2-IB treatment is combined with 36° C. targeted temperature management, also referred to in the art as controlled normothermia. As is known to a skilled person, 36° C. targeted temperature management is the active treatment of an individual in order to maintain a body temperature of around 36° C. Patients with an initially low temperature, for example, around 30° C., are actively re-warmed, preferably at a maximum rate of 0.5° C. per hour. Patients with a higher temperature (e.g., 38° C.) may be cooled, for example, using ice/cold water, ice cubes or mechanical cooling devices. 36° C. targeted temperature management differs from treatment with hypothermia in that an individual may require warming. Preferably, 36° C. targeted temperature management is used during the entire course of 2-IB treatment. For example, 36° C. targeted temperature management may be used for at least 20 hours, preferably at least 24 hours during 2-IB treatment.

In one aspect of the disclosure, methods are provided for the treatment of brain cell injury in an individual comprising administering to an individual in need thereof 2-IB in combination with hypothermia.

As used herein, the term "hypothermia" refers to subjecting a particular individual to hypothermic conditions, for example, by lowering the body or head temperature through passive or active techniques. Typically, subjecting to hypothermic conditions can lead to neuroprotection by decreasing the cell metabolism of body tissues.

In some embodiments, the core body temperature in a mammal is lowered by at least 1, 2, 3, 4, 5, 6, 7, 8, 9, or 10 degrees Celsius below the normal core body temperature for the mammal. In some embodiments, the core body temperature in a mammal is lowered by between 1-10, 2-6, or preferably 2-4 degrees Celsius below the normal core body temperature for the mammal.

In one preferred embodiment, the temperature of the mammal is maintained at a temperature of from about 31 degrees Celsius to about 37 degrees Celsius. More preferably, the temperature of the mammal is maintained at a temperature of from about 32 degrees Celsius to about 36 degrees Celsius more preferably from about 32 degrees Celsius to about 35 degrees Celsius, more preferably still, from about 33 degrees Celsius to about 34 degrees Celsius. As used herein, hypothermia refers to a core body temperature of 35 degrees Celsius or less. Typically, "hypothermic" conditions in an adult human refers to keeping the body temperature at around 33 degrees Celsius.

Induction of hypothermia by lowering of the core temperature of the body may be performed by any method known in the art. Typical hypothermia induction means in neonates use either whole body or head cooling, using the Olympic CoolCap™ system. In adults, it is preferred that hypothermia be induced using ice/cold water, ice cubes or mechanical cooling devices such as surface cooling, using the Tekotherm™; cooling blankets, and other commercially available cooling systems, including cooling using catheters placed in a large vessel. Alternatively, hypothermia may be induced using pharmaceutical agents such as, e.g., vanilloid receptor agonists, capsaicinoids or capsaicinoid-like agonists (described in US Patent Publication 20090197966, the content of which is hereby incorporated by reference) and neurotensin analogs capable of crossing the blood-brain barrier, such as NT69L and NT77 (described in U.S. Pat. No. 7,319,090, the content of which is hereby incorporated by reference).

Hypothermia and 2-IB may be administered simultaneously, sequentially, or separately. As used herein, "simultaneously" is used to mean that the 2-IB is administered concurrently with hypothermia, whereas the term "in combination" is used to mean the 2-IB is administered, if not simultaneously, then "sequentially" within a timeframe in which the 2-IB and the hypothermia both exhibit a therapeutic effect, i.e., they are both are available to act therapeutically within the same time-frame. Thus, administration "sequentially" may permit the 2-IB to be administered within 5 minutes, 10 minutes or a matter of hours before or after the hypothermia, provided the circulatory half-life of the 2-IB is such that it is present in a therapeutically effective amount when the subject is exposed to hypothermic conditions. In preferred embodiments, 2-IB is administered such that its effect is still present after the individual's body temperature has returned to normal.

In contrast to "in combination" or "sequentially," "separately" is used herein to mean that the gap between administering the 2-IB and exposing the subject to hypothermia is significant, i.e., the 2-IB may not yet or no longer be present in the bloodstream in a therapeutically effective amount when the subject is exposed to hypothermic conditions.

The present disclosure demonstrates that a combination of 2-IB and hypothermia has an improved effect on reducing hypoxia-induced cell damage over hypothermia treatment alone. The therapeutically effective dosage of 2-IB is therefore lower when combined with hypothermia. As described in Example 5C, the 2-IB dose may be decreased by 37% as compared to normothermic conditions. Accordingly, all dosages previously provided herein are suitable for use in combination with hypothermia, when the dose is decreased by 37% of the original dose.

Whereas the minimum dosage of 2-IB is 0.05 mg/kg/day, preferably at least 0.2 mg/kg/day; when combined with hypothermia, the minimum dosage may be reduced to 0.01/kg/day. More preferred dosages of 2-IB when combined with hypothermia include 0.05 to 10 mg/kg/day, 0.1 to 10 mg/kg/day, and 0.2 to 10 mg/kg/day. Other preferred dosages of 2-IB when combined with hypothermia include 0.05 to 5 mg/kg/day, 0.1 to 5 mg/kg/day, and 0.2 to 5 mg/kg/day. Other preferred dosages of 2-IB when combined with hypothermia include 0.05 to 1.5 mg/kg/day, 0.1 to 1.5 mg/kg/day, and 0.2 to 1.5 mg/kg/day. Other preferred dosages of 2-IB when combined with hypothermia include 0.05 to 1 mg/kg/day, 0.1 to 1 mg/kg/day, and 0.2 to 1 mg/kg/day. Other preferred dosages of 2-IB when combined with hypothermia include 0.05 to 0.5 mg/kg/day, 0.1 to 0.5 mg/kg/day, and 0.2 to 0.5 mg/kg/day. Especially preferred dosages include 0.03 to 3.7 mg/kg/day, 0.04 to 3.7 mg/kg/day, 0.04 to 4 mg/kg/day, 0.03 to 1.9 mg/kg/day, 0.4 to 1.9 mg/kg/day, 0.03 to 2 mg/kg/day, 0.04 to 2 mg/kg/day, 0.03 to 1.9 mg/kg/day, 0.04 to 1.9 mg/kg/day, 0.03 to 1 mg/kg/day, 0.04 to 1 mg/kg/day, 0.03 to 0.4 mg/kg/day and 0.04 to 0.4 mg/kg/day. In most preferred embodiments, 0.04 to 3.7 mg/kg/day of 2-iminobiotin is administered, preferably wherein between 0.04 to 1.9 mg.

As described in Example 5B, the disclosure provides that body weight has minimal effect on 2-IB exposure. In preferred embodiments, doses not influenced by weight may be provided. Preferably, the individuals treated with the doses independent of weight disclosed herein range from 20 to 200 kg, more preferably ranging from 30 kg to 180 kg.

Preferably, the total daily dose is between 2-40, more preferably between 3 to 30 mg, preferably between 6-29 mg, most preferably between 4-20 mg. Preferably, the daily dose is administered as at least three doses, i.e., at at least three separate time points; preferably between 3-10 doses. It is clear to a skilled person, that administration of at three doses or at least three separate time points encompasses continuous infusion. Preferably, the daily dose is administered as at least four doses, i.e., at at least four separate time points. Most preferably, the daily dose is administered as at least six doses, i.e., at at least six separate time points. It is clear to a skilled person that the time between each dose (or time point) should be essentially the same. Preferably, 2-IB is administered at a dosage of 1 mg, 1.5 mg, 2 mg, 2.5 mg, 3 mg, 3.5 mg, 4 mg, 4.5 mg, or 5 mg, when combined with hypothermia. In a non-limiting exemplary embodiment, an individual weighing 80 kg may receive four doses of 2-IB in a day in combination with hypothermia, wherein each dosage comprises between 1-5 mg. The individual would thus receive 0.01-0.06 mg/kg/dose and 0.06-0.23 mg/kg/day. Preferably, 2-IB is administered at a dosage of between 0.5-8 mg, preferably 0.7-7 mg, more preferably between 1-5 mg, preferably 4 times per day.

2-IB may be provided in any suitable pharmaceutically acceptable formulation. The disclosure provides solutions and dosage forms of 2-IB for, preferably, parenteral administration. Parental administration as used herein refers to modes of administration including, without limitation, intravenous, intramuscular, intraarterial, intrathecal, subdural, subarachnoidal, intracapsular, intraorbital, intracardiac, intradermal, intraperitoneal, transtracheal, subcutaneous, subcuticular, intraarticular, subcapsular, subarachnoid, intraspinal and intrasternal injection and infusion. 2-IB may also be administered orally, in particular in patients afflicted with brain injury from neurodegeneration, which may require long-term treatment.

2-IB may be in any form suitable for such administration, including but not limited to tablets, capsules, powders, sachets, solutions, suspensions, emulsions, elixirs, droplets, sprays, etc. These may be formulated in a manner known per se, optionally using one or more suitable pharmaceutically acceptable adjuvants, excipients or carriers; and may also be suitably packaged, e.g., in a suitable container such as a vial or a bottle.

Preferably, the pharmaceutical preparations are administered intravenously, such as by injection and in particular by (drip-)infusion, slow-bolus, or via a pump system. Preparations suitable for such intravenous administration may for instance be prepared by mixing 2-IB or a salt thereof with water or a pharmaceutically acceptable buffer or solution such as normal saline. In preferred embodiments, the fixed dosages described herein are provided as single unit dosage forms. For example, the disclosure provides a single unit dosage comprising 1 mg, 1.5 mg, 2 mg, 2.5 mg, 3 mg, 3.5 mg, 4 mg, 4.5 mg, or 5 mg, 6 mg, 7 mg, 8 mg, 9 mg, 10 mg, 11 mg, 12 mg, or 13 mg of 2-IB.

Preferred formulations include those described in WO 2011/149349, which is hereby incorporated by reference. For example, in some embodiments, suitable 2-IB formulations are in the form of an aqueous solution and comprise substituted beta-cyclodextrins, such as, e.g., hydroxypropyl-beta-cyclodextrin and sulfobutylether-beta-cyclodextrin. In some embodiments, suitable 2-IB formulations are in the form of an aqueous solution and include an acid buffer to adjust the pH within the range from about 4 to about 7. Preferably, the formulation comprises sufficient citric acid and/or sodium citrate or other citrate salt to reach the desired pH. In some embodiments, the formulations comprise between 1 and 25 mM citric acid. In some embodiments the formulations comprise between 0.1 and 5 mM sodium citrate. In some embodiments, the formulations comprise at least 20 mM citric acid/citrate.

Definitions

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, the additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

The invention is further explained in the following examples. These examples do not limit the scope of the invention, but merely serve to clarify the invention.

EXAMPLES

Example 1: 2-IB Reduces Hypoxia-Induced Neuronal Cell Damage In Vitro

There is a lack of knowledge concerning the 2-IB-mediated effects on cellular and molecular levels and the optimal 2-IB concentrations. The aim of this study was to validate possible neuroprotective effects of different 2-IB concentrations in-vitro and to explore the underlying cellular mechanisms.

Experimental Setting

In vitro hypoxia was induced in the cell cultures by using our recently described system with minor modifications (Huang et al., 2013b; Weber et al., 2015; Zitta et al., 2010). Enzyme stock solutions (100×) of catalase and glucose oxidase (both from Sigma-Aldrich) were prepared in cell culture medium (DMEM/F12, 1% FCS; final concentration: 120 U/ml and 2 U/ml respectively; Sigma-Aldrich) leading to a decrease of partial pressure of oxygen ($pO_2$) below 10 mmHg within 5 minutes. Hypoxic conditions were confirmed by using a tissue oxygen pressure monitor (LICOX® CMP Oxygen Catheter; Integra, Plainsboro, USA). After 7 hours of hypoxia, the cells were washed twice with PBS (PAA) and fresh normoxic medium supplemented with solvent (citrate buffer 1%) or 2-IB (10, 30, 50, 100 and 300 ng/mL) was added to the cells. Investigations of cell damage, metabolic activity, ROS, hydrogen peroxide, nitrite/nitrate production, erkl/2, akt and stat5 phosphorylation as well as cell stress protein expression were performed with cell culture media or cell protein (FIG. 1).

Lactate Dehydrogenase (LDH) Cytotoxicity Assays

The release of LDH from cultured cells into the medium was quantified by using a colorimetric cytotoxicity detection kit (Roche, Mannheim, Germany). Samples were prepared based on the manufacturer's protocol. Briefly, culture media were collected 24 hours after hypoxia and stored at −20° C. For evaluation of total LDH, cells were lysed with 2% TRITON® X-100 (Carl Roth, Karlsruhe, Germany) for 15 minutes at 37° C. LDH activity of the samples was measured in 96-well plates at 490 nm using an ELISA reader (Tecan, Crailsheim, Austria) in combination with the Magellan software v1.1.

Metabolic Activity Assays

Metabolically active cells were evaluated by using a colorimetric kit (CELLTITER96® AQueous One Solution Reagent G3580 Promega Madison, Wis., USA). Samples were prepared concerning to the manufacturer's protocol. Briefly, $4\times10^4$ cells were seeded per well in a 96-well plate with 100 µl DMEM/F12 supplemented with 10% FCS per well. After 2 days in culture, normoxia or hypoxia was applied for 7 hours followed by the addition of 2-IB or the respective solvent control (citrate 1%) for 17 hours. After that, 20 µl of MTT reagent were added to each well for 2.5 hours at 37° C. Metabolic active cells generate a colored product, the absorbance of which was measured at 490 nm using an ELISA reader (Tecan, Crailsheim, Austria) in combination with the Magellan software v1.1.

Measurements of Reactive Oxygen Species and Hydrogen Peroxide

For reactive oxygen species (ROS) measurements, $4\times10^4$ cells were seeded per well and cultured for 3 days in black walled 96-well plates (Greiner Bio-One, Frickenhausen, Germany). After hypoxia, cells were washed with pre-warmed PBS and cultured in a phenol red-free DMEM/F12 medium (Gibco®-invitrogen, NY, USA) with 1% fetal calf serum (PAA) for 17 hours, supplemented with solvent (citrate 1%) or 2-IB (10, 30, 50, 100, 300 ng/ml). Intracellular ROS were measured by adding 2'7'-dichlorodihydro-fluorescein diacetate (H2DCFDA, Sigma-Aldrich) to a final concentration of 10 µM which is oxidized to fluorescent dichlorofluorescein (DCF) by intracellular ROS. DCF-loaded cells were kept in the dark at 37° C. and fluorescence was evaluated at an excitation wavelength of 485 nm and emission wavelength of 535 nm using an ELISA reader (Genios F L; Tecan, Crailsheim, Austria). Fluorescence data were acquired at time points 0 (T0) and 30 minutes (T30) and results were calculated as the increment of fluorescence (%) over time [(T30-T0)/T0×100]. Hydrogen peroxide was measured in the culture medium with a Quanti-Chrom™ Peroxide Assay Kit (Bio-Assay Systems, Hayward, USA), which utilizes the chromogenic Fe3+-xylenol orange reaction, in which a purple complex is formed when Fe2+ provided in the reagent is oxidized to Fe3+ by the hydrogen peroxide present in the sample. Briefly, 100 µl of detection reagent were added to 20 µl of culture medium and measurements were performed based on the manufacturer's protocol. Absorbance of the colorimetric samples and standards was measured at 620 nm using an ELISA reader (Tecan, Crailsheim, Germany).

Nitrate/Nitrite Assays

Nitrate and nitrite concentrations were evaluated in culture media using a Griess colorimetric assay kit (Sigma-Aldrich) according to the manufacturer's instructions. Absorbance at 540 nm was measured in samples and standards using an ELISA reader (Tecan, Crailsheim, Germany).

Protein Isolation and Western Blotting

Protein extraction was performed using RIPA buffer containing 150 mM sodium chloride, 1% NP-40, 1% sodium deoxycholate, 0.1% sodium dodecyl sulfate (SDS) and 50 mM Tris-HCl buffer (pH 7.6; all from Sigma-Aldrich) or alternatively M-PER buffer (Mammalian Protein Extraction Reagent; Pierce, Ill., USA). Protein concentrations were determined with Roti®-Quant assays (Carl Roth) and samples were stored at −20° C. until use. For Western blotting, 30 µg of total protein were mixed with 4× Laemmli buffer (8% SDS, 40% glycerol, 20% 2-mercaptoethanol, 0.008% bromphenol blue, 0.25 M Tris-HCl, all from Sigma-Aldrich) and incubated for 3 minutes at 95° C. Samples were separated by electrophoresis in 10% SDS-PAGE gels and transferred onto a PVDF membrane (Amersham Pharmacia Biotech, Piscataway, USA). After blocking 1 hour in TBST with 3% BSA at room temperature, the membranes were incubated at 4° C. overnight with specific primary antibodies for phosphorylated erkl/2 (Cell signaling technology; 1:8,000), erkl/2 (Cell signaling technology; 1:8,000), phosphorylated akt (Cell signaling technology; 1:1,000), akt (Cell signaling technology; 1:2,000), phosphorylated stat5 (R&D Systems, Minneapolis, USA; 1:200) and stat5 (R&D Systems, Minneapolis, USA; 1:200). After washing in TBST buffer, the membranes were incubated for 1 hour with peroxidase-conjugated swine anti-rabbit immunoglobulin G (Dako, Hamburg, Germany; 1:20,000) using the manufacturer's instructions. The final reaction was visualized using enhanced chemiluminescence (ECL-Plus Western Blotting Detection Reagents; Amersham Pharmacia Biotech, Buckinghamshire, UK), and the membranes were exposed to X-ray films. Images were taken and densitometrically analyzed with the software ImageJ (v1.41o, NIH).

Cell Stress Proteome Profiler Arrays

Proteome profiling was performed using commercially available cell stress proteome profiler arrays (R&D Systems, Minneapolis, USA) and the manufacturer's protocol provided with the assay kit. Equal amounts (50 μg) of protein from each experiment (N=4) were pooled and applied to the respective array membrane. Expression levels of 26 cell stress associated proteins were evaluated by densitometric analyses of the arrays using the ImageJ 1.410 software (ImageJ, NIH, USA).

Statistical Analysis

Statistical analyses were performed using GraphPad Prism 5 (GraphPad Software, San Diego, USA). All experiments were independently performed 5 times using at least duplicate samples in each experiment. Exceptions were: (i) stress proteome profiler arrays in which samples of 4 experiments were pooled and (ii) Western blotting studies which were independently performed 3 times. Data are presented as mean values with standard deviations (SD). Statistical comparisons were performed using Student's t-tests, one-way ANOVA (for intra group comparisons) and two-way ANOVA (for inter group comparisons) with Bonferroni post-tests. Differences were considered to be statistically significant if p was less than 0.05. Non-parametric data were analyzed by Kruskal-Wallis test and Dunns post-test. For parametric tests analyses, data were transformed (arcsin of square root of x) to obtain normality.

Results

2-IB Reduces Hypoxia-Induced Cell Damage and Increases Metabolic Activity

Figure 2A:
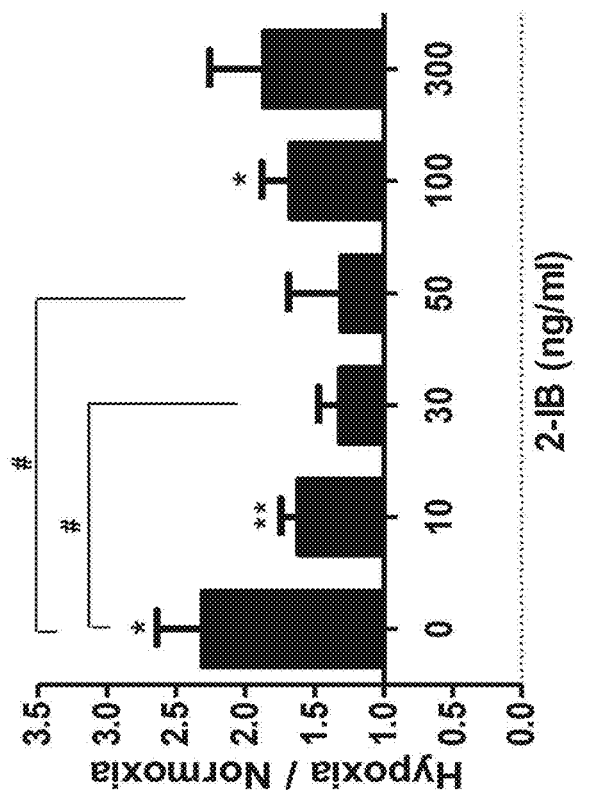
Figure 2B:
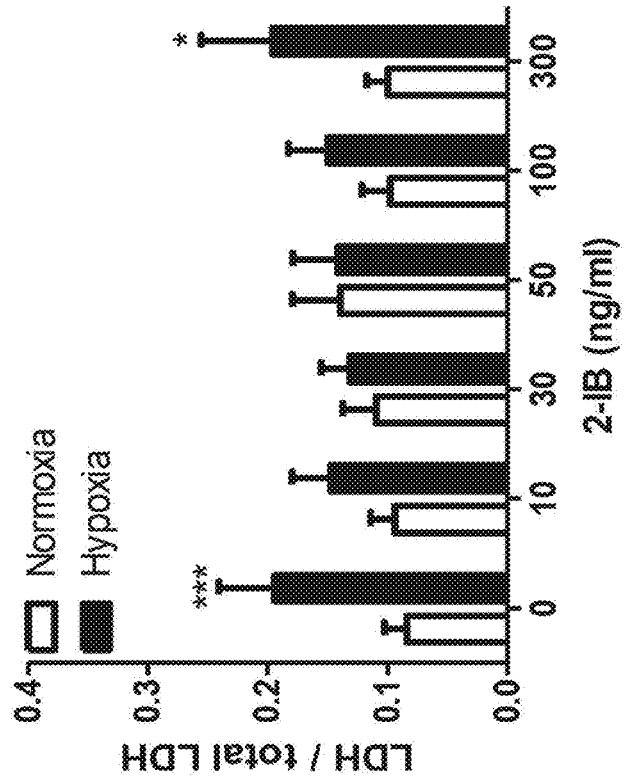

Compared to normoxia, cell damage was significantly increased 17 hours after hypoxia (LDH/total LDH: normoxia: $0.08\pm0.02$; hypoxia: $0.19\pm0.05$, $P<0.001$; FIG. 2A). Addition of 2-IB in the range between 10 and 100 ng/ml reduced the hypoxia-induced LDH release to levels found under normoxic conditions (10 ng/ml 2-IB, normoxia: $0.09\pm0.02$; hypoxia: $0.15\pm0.03$; $P>0.05$. 30 ng/ml 2-IB, normoxia: $0.11\pm0.03$; hypoxia: $0.13\pm0.02$; $P>0.05$. 50 ng/ml 2-IB, normoxia: $0.14\pm0.04$; hypoxia: $0.14\pm0.04$; $P>0.05$. 100 ng/ml 2-IB, normoxia: $0.10\pm0.02$; hypoxia: $0.15\pm0.03$; $P>0.05$ FIG. 2A). This effect was not observed at higher concentrations of 2-IB (300 ng/ml 2-IB, normoxia: $0.10\pm0.02$; hypoxia: $0.20\pm0.06$; $P<0.05$; FIG. 2A). Concerning the reduction of hypoxia-induced cell damage, 30 and 50 ng/ml 2-IB were the most effective concentrations ($P<0.05$ vs. control; FIG. 2B).

MTS assays revealed a significantly reduced metabolic activity of IMR-32 cells 17 hours after hypoxia compared to cells grown under normoxic conditions (metabolic activity (a.u.): normoxia: $0.61\pm0.09$; hypoxia: $0.33\pm0.07$; $P<0.01$; FIG. 2C). Addition of 2-IB in the range between 10 and 50 ng/ml attenuated the hypoxia-mediated reduction of metabolic activity to levels found under normoxic conditions (metabolic activity (a.u.): 10 ng/ml 2-IB, normoxia: $0.44\pm0.08$; hypoxia: $0.44\pm0.10$; $P>0.05$; 30 ng/ml 2-IB, normoxia: $0.49\pm0.08$, hypoxia: $0.45\pm0.09$; $P>0.05$; 50 ng/ml 2-IB, normoxia: $0.50\pm0.08$; hypoxia: $0.41\pm0.06$; $P>0.05$; FIG. 2C), while higher concentrations of 2-IB (100 and 300 ng/ml) were not effective (metabolic activity (a.u.): 100 ng/ml 2-IB, normoxia: $0.58\pm0.09$; hypoxia: $0.33\pm0.06$; $P<0.05$. 300 ng/ml 2-IB, normoxia: $0.63\pm0.09$; hypoxia: $0.33\pm0.07$; $P<0.01$; FIG. 2C). Hypoxia-induced reduction of metabolic activity was most efficiently counteracted by 10, 30 and 50 ng/ml 2-IB ($P<0.01$ vs. control; FIG. 2D).

2-Iminobiotin Reduces Hypoxia-Induced Production of Reactive Oxygen Species

Figures 3A, 3B:
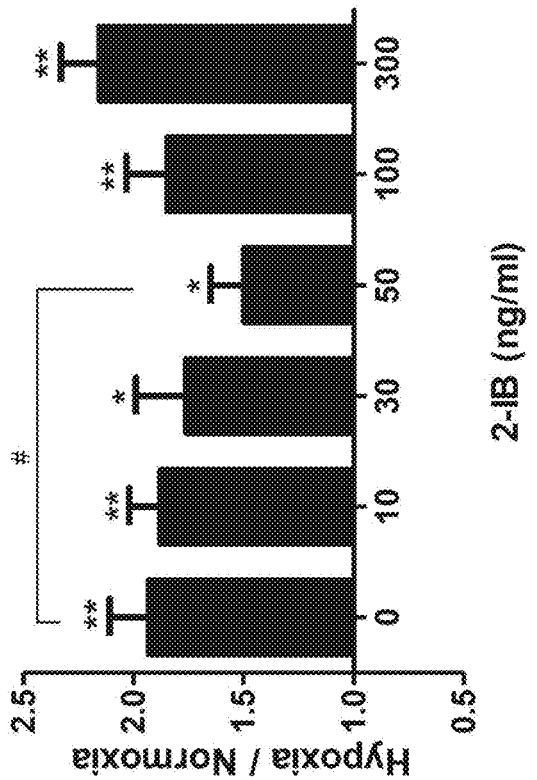
FIGS. 3A and 3B: Effects of 2-IB on hypoxia-induced production of reactive oxygen species (ROS). 2-IB attenuates hypoxia-induced ROS production (FIGS. 3A and 3B) showing a U-shaped dose response curve. Columns display the mean; bars denote SD.

The production of reactive oxygen species (ROS) was significantly increased under hypoxic conditions (ROS increase (T30-T0)/T0×100: normoxia: $129.18\pm26.92$; hypoxia: $248.02\pm59.24$; $P<0.05$; FIG. 3A). Low doses of 2-IB (30 and 50 ng/ml) attenuated the hypoxia-induced ROS production to levels not significantly different from those found under normoxic conditions (ROS increase (T30–T0)/T0×100: 30 ng/ml 2-IB, normoxia: $118.93\pm20.09$; hypoxia: $222.00\pm52.57$; $P>0.05$. 50 ng/ml 2-IB, normoxia: $154.85\pm30.83$; hypoxia: $233.38\pm53.94$; $P>0.05$; FIG. 3A), while higher concentrations of 2-IB were not effective (ROS increase (T30-T0)/T0×100: 100 ng/ml 2-IB, normoxia: $128.84\pm21.94$; hypoxia: $246.71\pm58.94$; $P<0.05$. 300 ng/ml 2-IB, normoxia: $141.20\pm25.35$; hypoxia: $311.57\pm79.02$; $P<0.01$; FIG. 3A). Hypoxia-induced generation of ROS was most efficiently attenuated with 50 ng/ml 2-IB FIG. 3B). Hypoxia also resulted in a dramatic increase of hydrogen peroxide production (hypoxia: $19.01\pm2.61$ M; normoxia: $0.10\pm0.07$ M; $P<0.001$). However, addition of 30 ng/ml 2-IB did not attenuate the hypoxia-induced release of hydrogen peroxide (data not shown), although this concentration of 2-IB was cell protective and attenuated hypoxia-induced ROS production (FIGS. 2A, 2B and 3A, 3B). Regarding nitrate and nitrite which can form NO and other bioactive nitrogen oxides (Kaandorp et al., 2010), colorimetric measurements revealed that culture media of IMR-32 cells contained only very low concentrations of both molecules (<5 μM) and that neither nitrate nor nitrite concentrations were influenced by hypoxia or by 2-IB (data not shown).

Figure 4:
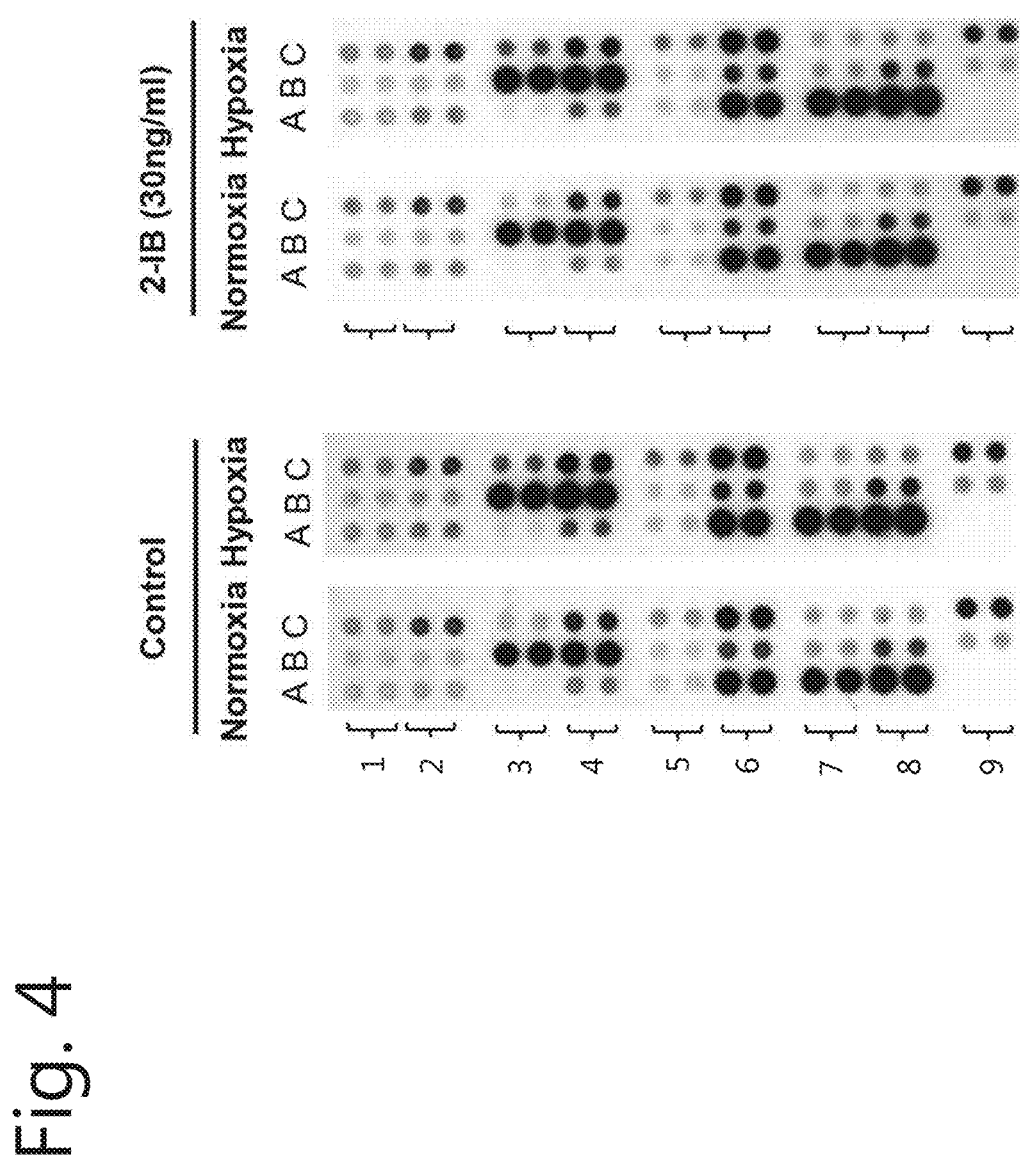
FIG. 4: Regulation of cell stress-associated proteins by 2-IB. Application of 2-IB after the hypoxic insult attenuates the hypoxia-induced expression of cell stress proteins and leads to an increase in the numbers of down-regulated proteins and proteins that remain unchanged. Proteome profiling array: 1A pp38α, phospho-p38 alpha (T181/Y185); 1B HIF2α, hypoxia inducible factor 2 alpha; 1C ADAMTS 1, a disintegrin and metalloproteinase with thrombospondin motifs 1; 2A pp53, phospho-p53 (S46); 2B pHSP-27, phospho heat shock protein-27; 2C Bcl-2, B cell lymphoma-2; 3A PON1, paraoxonase 1; 3B HSP-60, heat shock protein-60; 3C CA IX, carbonic anhydrase IX; 4A PON2, paraoxonase 2;4B HSP-70, heat shock protein-70; 4C Cited2, Cbp/p300-interacting transactivator; 4A PON3, paraoxonase 3; 5B IDO, indoleamine 5C 2,3-dioxygenase; COX-2, cyclooxygenase-2; 6A Thio-1, thioredoxin-1;6B pJNK, phospho c-Jun n-terminal kinase (T183/Y185); 6C CytC, cytochrome C; 7A SIRT2, sirtuin 2; 7B NFkB1, nuclear factor kappa B1;7C Dkk-4, dickkopf-4; 8A SOD2, superoxide dismutase 2; 8B p21/CIP1, cyclin-dependent kinase inhibitor 1A; 8C FABP-1, fatty acid binding protein-1; 9A—Ctr, negative control; 9B p27, cyclin-dependent kinase inhibitor 1B; 9C HIF1α, hypoxia inducible factor 1.

Hypoxia-Induced Expression of Cell Stress-Associated Proteins is Attenuated by 2-IB Cell stress proteome profiling arrays revealed an up regulation of 23/26 (88%) cell stress associated proteins after hypoxia, while only 1/26 (4%) was down regulated and 2/26 (8%) were unchanged. Application of 30 ng/ml of 2-IB after the hypoxic insult attenuated the hypoxia-induced expression of cell stress proteins to 19/26 (73%) up regulated proteins and resulted in an increase in the numbers of down regulated proteins 3/26 (12%) and proteins that remained unchanged 4/26 (15%; FIG. 4). A detailed analysis of the investigated proteins is depicted in Table 1.

TABLE 1

Analysis of proteome profiling of cell stress proteins. Numbers in the table represent the mean densitometric intensities of duplicate sample spots.

| | Control | | 2-IB (30 ng/ml) | |
|---|---|---|---|---|
| | Normoxia | Hypoxia | Normoxia | Hypoxia |
| ADAMTS1 | 10.40 | 13.91 | 10.32 | 9.23 |
| Bcl-2 | 36.45 | 41.58 | 32.27 | 42.62 |
| CA IX | 1.98 | 24.77 | 0.00 | 23.02 |
| Cited 2 | 48.22 | 84.45 | 44.07 | 67.91 |
| COX-2 | 6.63 | 15.45 | 8.91 | 13.79 |
| Cytochrome C | 90.93 | 105.25 | 84.87 | 108.04 |
| Dkk-4 | 3.62 | 4.16 | 2.81 | 3.47 |
| FABP-1 | 4.59 | 10.70 | 6.67 | 9.02 |
| HIF1a | 59.32 | 48.76 | 62.15 | 47.93 |
| HIF2a | 0.65 | 4.29 | 0.00 | 0.00 |
| pHSP-27 | 0.52 | 7.09 | 0.79 | 1.65 |

TABLE 1-continued

Analysis of proteome profiling of cell stress proteins.
Numbers in the table represent the mean densitometric
intensities of duplicate sample spots.

|  | Control | | 2-IB (30 ng/ml) | |
| --- | --- | --- | --- | --- |
|  | Normoxia | Hypoxia | Normoxia | Hypoxia |
| HSP60 | 111.44 | 155.84 | 121.73 | 150.57 |
| HSP70 | 129.20 | 186.32 | 139.78 | 170.82 |
| IDO | 0.00 | 0.00 | 0.00 | 0.00 |
| pJNK | 33.98 | 53.09 | 39.24 | 48.63 |
| NFkB1 | 5.51 | 7.87 | 6.09 | 8.63 |
| p21/CIP1 | 34.64 | 54.17 | 43.13 | 51.41 |
| p27 | 3.18 | 8.04 | 4.51 | 4.67 |
| pp38a | 3.27 | 9.13 | 4.72 | 3.52 |
| PP53 | 4.45 | 15.91 | 8.64 | 11.92 |
| PON1 | 0.00 | 0.00 | 0.00 | 0.00 |
| PON2 | 13.06 | 28.13 | 8.83 | 20.16 |
| PON3 | 0.00 | 1.01 | 0.00 | 0.00 |
| Thioredoxin-1 | 123.14 | 152.74 | 126.34 | 147.57 |
| SIRT2 | 117.52 | 160.47 | 148.80 | 171.53 |
| SOD2 | 158.08 | 195.06 | 181.53 | 203.11 |

2-Iminobiotin Increases the Phosphorylation of the Pro-Survival Molecule Akt

Figure 5:
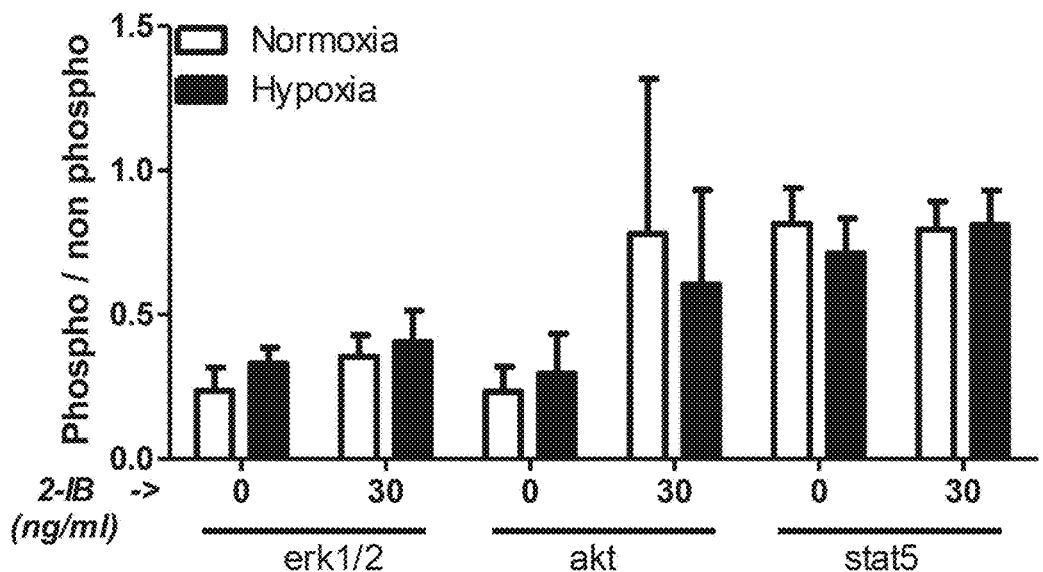
FIG. 5: Phosphorylation of key signaling molecules. 2-IB leads to a by trend increased phosphorylation of the pro-survival molecule akt under normoxic and hypoxic conditions. Columns display the mean; bars denote SD. N, normoxia; H, hypoxia.

2-IB (30 ng/ml) did not influence the phosphorylation of erkl/2 and stat5. However, a by trend increased phosphorylation of the pro-survival molecule akt was detected under normoxic and hypoxic conditions (phospho akt/akt, normoxia: 0.23±0.09; phospho akt/akt, hypoxia: 0.29±0.14; phospho akt/akt, normoxia plus 30 ng/ml 2-IB: 0.78±0.54; phospho akt/akt, hypoxia plus 30 ng/ml 2-IB: 0.60±0.33; $P>0.05$; FIG. 5)

Discussion

2-IB is a reversible inhibitor of NO biosynthesis, blocking mainly iNOS and nNOS activity (Tataranno et al., 2015). However, the cellular effects of 2-IB may not only be restricted to NOS regulation and several authors have suggested the involvement of NOS-independent pathways of 2-IB action (Nijboer et al., 2008; Tataranno et al., 2015; van den Tweel et al., 2005; van Kesteren et al., 2006).

Here we employed a human neuronal cell culture model of IMR-32 cells to evaluate possible neuroprotective effects of 2-IB in vitro, to explore the underlying cellular mechanisms and to determine the optimal neuroprotective concentrations of 2-IB. IMR-32 cells express only marginal amounts of NOS (mRNA, protein and NOS activity) (Fujisawa et al., 1994). These findings are confirmed by our data, which show low concentrations of nitrate and nitrite in culture media of IMR-32 cells. As the sum of nitrate and nitrite correlates well with the amount of total NO (Kaandorp et al., 2010), our data suggest low NO concentrations and NOS activities in IMR-32 cultures, classifying IMR-32 as a suitable model for the investigation of NOS-independent, 2-IB-mediated mechanisms.

In-vivo, hypoxic/ischemic injury results in a rapid loss of high-energy phosphate compounds and generalized depolarization, which induces release of glutamate and opening of both voltage-dependent and glutamate-regulated calcium channels, resulting in a large increase in cytosolic Ca2+ concentrations (White et al., 2000). This Ca2+ increase triggers a cascade of events which finally lead to neuronal cell degeneration (Perrone et al., 2013). In a first approach, employing our recently described in-vitro enzymatic hypoxia system (Huang et al., 2013a; Huang et al., 2013b; Hummitzsch et al., 2014; Weber et al., 2015; Zitta et al., 2012), IMR-32 cells were subjected to 7 hours of hypoxia, which resulted in significantly increased cell damage, reduction of metabolic activity and accumulation of ROS in the culture medium. Incubating the cultures with different concentrations of 2-IB for 24 hours after the hypoxic insult attenuated the hypoxia-induced cell damage, increased metabolic cell activity and reduced the production of ROS, while the hypoxia-mediated increase in hydrogen peroxide was not affected by 2-IB. Interestingly, our results revealed that culture media concentrations of 2-IB in the range between 30 ng/ml and 50 ng/ml were most effective in reducing hypoxia-induced cell damage in-vitro. Higher or lower concentrations of 2-IB were either not effective or showed adverse effects.

Concerning cell damage, metabolic activity and ROS production, the results of our study showed a U-shaped dose response relationship which has been documented in numerous biological, toxicological, and pharmacological investigations (Calabrese and Baldwin, 2001).

Based on the abovementioned findings that low concentrations of 2-IB protected from hypoxia-induced cell damage, we decided to further investigate potential additional mode of actions of 2-IB. Cell stress proteome profiling was performed and revealed that hypoxia upregulated 88% of the investigated stress proteins, while only 73% were up regulated after incubating the cells with 30 ng/ml 2-IB for 4 hours post hypoxia. One of the major indicators of cell stress are ROS (Moretti et al., 2015) and several studies have demonstrated a protective effect of antioxidant drugs against cell stress and apoptosis after cerebral ischemia and reperfusion (Perrone et al., 2013). 2-IB possesses antioxidant functions (Fan and Van Bel, 2010; Peeters-Scholte et al., 2002) and we also showed a moderate reduction of hypoxia-induced ROS production by 2-IB. Hypoxia and 2-IB-mediated changes in cell stress protein expression were detectable as early as 4 hours after the end of hypoxia, while significant changes in ROS occurred 17 hours after hypoxia. We therefore believe that ROS production represents a consequence of hypoxia-induced cell stress and that the 2-IB-mediated reduction of ROS is possibly indirectly achieved by an early reduction of cell stress protein expression. The hypothesis that 2-IB attenuates ROS production indirectly by the regulation of cell stress proteins is also supported by the fact that no direct antioxidant functions of 2-IB have been described so far.

Finally, cell stress and apoptosis are tightly associated (Mendez-Armenta et al., 2014; Rodrigo et al., 2013) and the phosphorylation of the cell signaling molecules akt and erk has been described to induce anti-apoptotic pathways (Jalsrai et al., 2014; Zhang et al., 2014). We observed a trend towards increased phosphorylation of akt after the addition of 30 ng/ml 2-IB, which was found under hypoxic as well as under normoxic conditions. Akt activation can also be achieved by different sirtuin (SIRT) isoforms (Pillai et al., 2014) and our cell stress array results showed an increased expression of SIRT2 after the addition of 2-IB under normoxic and hypoxic conditions, suggesting that 2-IB-mediated pathways may involve phosphorylation of akt and/or expression of sirtuins.

Taken together we show that hypoxia-induced neuronal cell damage is inhibited by low concentrations of 2-IB and that the associated mechanisms may involve ROS and a down-regulation of stress-associated protein expression.

REFERENCES

Bjorkman, S. T., Foster, K. A., O'Driscoll S, M., Healy, G. N., Lingwood, B. E., Burke, C., Colditz, P. B., 2006.

Hypoxic/Ischemic models in newborn piglet: comparison of constant FiO2 versus variable FiO2 delivery. Brain Res. 1100, 110-7.

Bringas-Grande, A., Fernandez-Luque, A., Garcia-Alfaro, C., Barrera-Chacon, M., Toledo-Gonzalez, M., Dominguez-Rolda, J. M., 2002. [Cerebral palsy in childhood: 250 cases report]. Rev. Neurol. 35, 812-7.

Calabrese, E. J., Baldwin, L. A., Holland, C. D., 1999. Hormesis: a highly generalizable and reproducible phenomenon with important implications for risk assessment. Risk Anal. 19, 261-81.

Calabrese, E. J., Baldwin, L. A., 2001. U-shaped dose-responses in biology, toxicology, and public health. Annu. Rev. Public Health. 22, 15-33.

Dursun, A., Okumus, N., Zenciroglu, A., 2012. Ischemia-modified albumin (IMA): could it be useful to predict perinatal asphyxia? J. Matern. Fetal Neonatal Med. 25, 2401-5.

Ekwochi, U., Ndu, I. K., Nwokoye, I. C., Ezenwosu, O. U., Amadi, O. F., Osuorah, D., 2014. Pattern of morbidity and mortality of newborns admitted into the sick and special care baby unit of Enugu State University Teaching Hospital, Enugu state. Niger. J. Clin. Pract. 17, 346-51.

Fan, X., van Bel, F., 2010. Pharmacological neuroprotection after perinatal asphyxia. J. Matern. Fetal Neonatal Med. 23 Suppl 3, 17-9.

Fujisawa, H., Ogura, T., Kurashima, Y., Yokoyama, T., Yamashita, J., Esumi, H., 1994. Expression of two types of nitric oxide synthase mRNA in human neuroblastoma cell lines. J. Neurochem. 63, 140-5.

Gulczynska, E., Gadzinowski, J., 2012. [Therapeutic hypothermia for neonatal hypoxic-ischemic encephalopathy]. Ginekol. Pol. 83, 214-8.

Gunn, A. J., Thoresen, M., 2006. Hypothermic neuroprotection. NeuroRx. 3, 154-69.

Hassell, K. J., Ezzati, M., Alonso-Alconada, D., Hausenloy, D. J., Robertson, N. J., 2015. New horizons for newborn brain protection: enhancing endogenous neuroprotection. Arch. Dis. Child Fetal Neonatal Ed.

Huang, Y., Zitta, K., Bein, B., Scholz, J., Steinfath, M., Albrecht, M., 2013a. Effect of propofol on hypoxia re-oxygenation induced neuronal cell damage in vitro*. Anaesthesia. 68, 31-9.

Huang, Y., Zitta, K., Bein, B., Steinfath, M., Albrecht, M., 2013b. An insert-based enzymatic cell culture system to rapidly and reversibly induce hypoxia: investigations of hypoxia-induced cell damage, protein expression and phosphorylation in neuronal IMR-32 cells. Dis. Model Mech. 6, 1507-14.

Hummitzsch, L., Zitta, K., Bein, B., Steinfath, M., Albrecht, M., 2014. Culture media from hypoxia conditioned endothelial cells protect human intestinal cells from hypoxia/reoxygenation injury. Exp. Cell Res. 322, 62-70.

Jalsrai, A., Numakawa, T., Ooshima, Y., Adachi, N., Kunugi, H., 2014. Phosphatase-mediated intracellular signaling contributes to neuroprotection by flavonoids of Iris tenuifolia. Am. J. Chin. Med. 42, 119-30.

Kaandorp, J. J., Benders, M. J., Rademaker, C. M., Torrance, H. L., Oudijk, M. A., de Haan, T. R., Bloemenkamp, K. W., Rijken, M., van Pampus, M. G., Bos, A. F., Porath, M. M., Oetomo, S. B., Willekes, C., Gavilanes, A. W., Wouters, M. G., van Elburg, R. M., Huisjes, A. J., Bakker, S. C., van Meir, C. A., von Lindern, J., Boon, J., de Boer, I. P., Rijnders, R. J., Jacobs, C. J., Uiterwaal, C. S., Mol, B. W., Visser, G. H., van Bel, F., Derks, J. B., 2010. Antenatal allopurinol for reduction of birth asphyxia induced brain damage (ALLO-Trial); a randomized double blind placebo controlled multicenter study. BMC Pregnancy Childbirth. 10, 8.

Koc, O., Kavuncuoglu, S., Ramoglu, M., Aldemir, E., Aktalay, A., Eras, Z., 2015. School Performance and Neurodevelopment of Very Low Birth Weight Preterm Infants: First Report From Turkey. J. Child Neurol.

Liu, L., Oza, S., Hogan, D., Perin, J., Rudan, I., Lawn, J. E., Cousens, S., Mathers, C., Black, R. E., 2015. Global, regional, and national causes of child mortality in 2000-13, with projections to inform post-2015 priorities: an updated systematic analysis. Lancet. 385, 430-40.

Maneru, C., Junque, C., 2002. [Cognitive deficit in perinatal asphyxia]. Rev. Neurol. 34, 1171-7.

Mendez-Armenta, M., Nava-Ruiz, C., Juarez-Rebollar, D., Rodriguez-Martinez, E., Gomez, P. Y., 2014. Oxidative stress associated with neuronal apoptosis in experimental models of epilepsy. Oxid. Med. Cell. Longev. 2014, 293689.

Moretti, R., Pansiot, J., Bettati, D., Strazielle, N., Ghersi-Egea, J. F., Damante, G., Fleiss, B., Titomanlio, L., Gressens, P., 2015. Blood-brain barrier dysfunction in disorders of the developing brain. Front. Neurosci. 9, 40.

Nabieva, T. N., 2009. [Neurological consequences following perinatal asphyxia in preschool age children]. Usp. Fiziol. Nauk. 40, 72-7.

Nijboer, C. H., Groenendaal, F., Kavelaars, A., Hagberg, H. H., van Bel, F., Heijnen, C. J., 2007. Gender-specific neuroprotection by 2-iminobiotin after hypoxia-ischemia in the neonatal rat via a nitric oxide independent pathway. J. Cereb. Blood Flow Metab. 27, 282-92.

Nijboer, C. H., Heijnen, C. J., Groenendaal, F., May, M. J., van Bel, F., Kavelaars, A., 2008. Strong neuroprotection by inhibition of NF-kappaB after neonatal hypoxia-ischemia involves apoptotic mechanisms but is independent of cytokines. Stroke. 39, 2129-37.

Peeters-Scholte, C., Koster, J., Veldhuis, W., van den Tweel, E., Zhu, C., Kops, N., Blomgren, K., Bar, D., van Buul-Offers, S., Hagberg, H., Nicolay, K., van Bel, F., Groenendaal, F., 2002. Neuroprotection by selective nitric oxide synthase inhibition at 24 hours after perinatal hypoxia-ischemia. Stroke. 33, 2304-10.

Peeters-Scholte, C., van den Tweel, E., Groenendaal, F., van Bel, F., 2004. Redox state of near infrared spectroscopy-measured cytochrome aa(3) correlates with delayed cerebral energy failure following perinatal hypoxia-ischaemia in the newborn pig. Exp. Brain Res. 156, 20-6.

Perrone, S., Santacroce, A., Buonocore, G., 2013. 2-Iminobiotin for the treatment of perinatal asphyxia. Expert Opinion on Orphan Drugs. 1, 935-945.

Pillai, V. B., Sundaresan, N. R., Gupta, M. P., 2014. Regulation of Akt signaling by sirtuins: its implication in cardiac hypertrophy and aging. Circ. Res. 114, 368-78.

Robertson, N. J., Faulkner, S., Fleiss, B., Bainbridge, A., Andorka, C., Price, D., Powell, E., Lecky-Thompson, L., Thei, L., Chandrasekaran, M., Hristova, M., Cady, E. B., Gressens, P., Golay, X., Raivich, G., 2013. Melatonin augments hypothermic neuroprotection in a perinatal asphyxia model. Brain. 136, 90-105.

Rodrigo, R., Libuy, M., Feliu, F., Hasson, D., 2013. Oxidative stress-related biomarkers in essential hypertension and ischemia-reperfusion myocardial damage. Dis. Markers. 35, 773-90.

Selway, L. D., 2010. State of the science: hypoxic ischemic encephalopathy and hypothermic intervention for neonates. Adv. Neonatal Care. 10, 60-6; quiz 67-8.

Tataranno, M. L., Perrone, S., Longini, M., Buonocore, G., 2015. New antioxidant drugs for neonatal brain injury. Oxid. Med. Cell Longev. 2015, 108251.

van den Tweel, E. R., van Bel, F., Kavelaars, A., Peeters-Scholte, C. M., Haumann, J., Nijboer, C. H., Heijnen, C. J., Groenendaal, F., 2005. Long-term neuroprotection with 2-iminobiotin, an inhibitor of neuronal and inducible nitric oxide synthase, after cerebral hypoxia-ischemia in neonatal rats. J. Cereb. Blood Flow Metab. 25, 67-74.

van Kesteren, C., Benders, M. J., Groenendaal, F., van Bel, F., Ververs, F. F., Rademaker, C. M., 2006. Population pharmacokinetics of allopurinol in full-term neonates with perinatal asphyx ia. Ther. Drug Monit. 28, 339-44.

Weber, N. C., Riedemann, I., Smit, K. F., Zitta, K., van de Vondervoort, D., Zuurbier, C. J., Hollmann, M. W., Preckel, B., Albrecht, M., 2015. Plasma from human volunteers subjected to remote ischemic preconditioning protects human endothelial cells from hypoxia-induced cell damage. Basic Res. Cardiol. 110, 17.

White, B. C., Sullivan, J. M., DeGracia, D. J., O'Neil, B. J., Neumar, R. W., Grossman, L. I., Rafols, J. A., Krause, G. S., 2000. Brain ischemia and reperfusion: molecular mechanisms of neuronal injury. J. Neurol. Sci. 179, 1-33.

Zhang, J., Wang, Q., Xiang, H., Xin, Y., Chang, M., Lu, H., 2014. Neuroprotection with erythropoietin in preterm and/or low birth weight infants. J. Clin. Neurosci. 21, 1283-7.

Zhu, C., Wang, X., Qiu, L., Peeters-Scholte, C., Hagberg, H., Blomgren, K., 2004. Nitrosylation precedes caspase-3 activation and translocation of apoptosis-inducing factor in neonatal rat cerebral hypoxia-ischaemia. J. Neurochem. 90, 462-71.

Zitta, K., Meybohm, P., Bein, B., Ohnesorge, H., Steinfath, M., Scholz, J., Albrecht, M., 2010. Cytoprotective effects of the volatile anesthetic sevoflurane are highly dependent on timing and duration of sevoflurane conditioning: findings from a human, in-vitro hypoxia model. Eur. J. Pharmacol. 645, 39-46.

Zitta, K., Meybohm, P., Bein, B., Heinrich, C., Renner, J., Cremer, J., Steinfath, M., Scholz, J., Albrecht, M., 2012. Serum from patients undergoing remote ischemic preconditioning protects cultured human intestinal cells from hypoxia-induced damage: involvement of matrixmetalloproteinase-2 and -9. Mol. Med. 18, 29-37.

Ferriero et al., J. Anat. 217:429, 2010

Ben-ari et al., Neuroscientist 18:467; 2012

Vannucci et al., J. Exp. Bio. 207:3149, 2004

Kilb W. Development of the GABAergic system from birth to adolescence. Neuroscientist. 2012 December; 18(6): 613-30

Haynes R. L., Borenstein N. S., Desilva T. M., Folkerth R. D., Liu L. G., Volpe J. J., Kinney H. C. Axonal development in the cerebral white matter of the human fetus and infant. J. Comp. Neurol. 2005 Apr. 4; 484(2):156-67.)

Saunders et al., Cellular and Molecular Neurobiology 20:29, 2000

Lopez D F, Faustino J, Daneman R, et al. Blood-brain barrier permeability is increased after acute adult stroke but not neonatal stroke in the rat. The Journal of Neuroscience 2012; 32(28):9588-9600

Saunders et al., Frontiers in Pharmacology 3:1, 2012

Mulberg et al., Pediatric Drug Development: Concepts and Applications; Chpt 20, 2009

Example 2: Combination Treatment of 2-IB and Hypothermia In Vitro

We have shown that the biotin analogue 2-iminobiotin (2-IB) is able to reduce neuronal cell damage. Here we evaluated whether 2-IB has the potential to attenuate hypoxia-induced neuronal cell damage also under conditions of mild-hypothermia.

Methods:

In-vitro hypoxia was induced for 7 hours using IMR-32 cell cultures. After the hypoxic insult, cultures were subjected to 25 hours of mild hypothermia (33.5° C.) and were incubated with or without 2-IB (10, 30, 50, 100 and 300 ng/ml). Cell morphology was evaluated by brightfield microscopy and cell damage was analyzed by LDH assays. Production of reactive oxygen species (ROS) was measured using fluorometric assays. Western blotting for PARP and phosphorylated as well as unphosphorylated akt and erkl/2 was performed.

Figure 6:
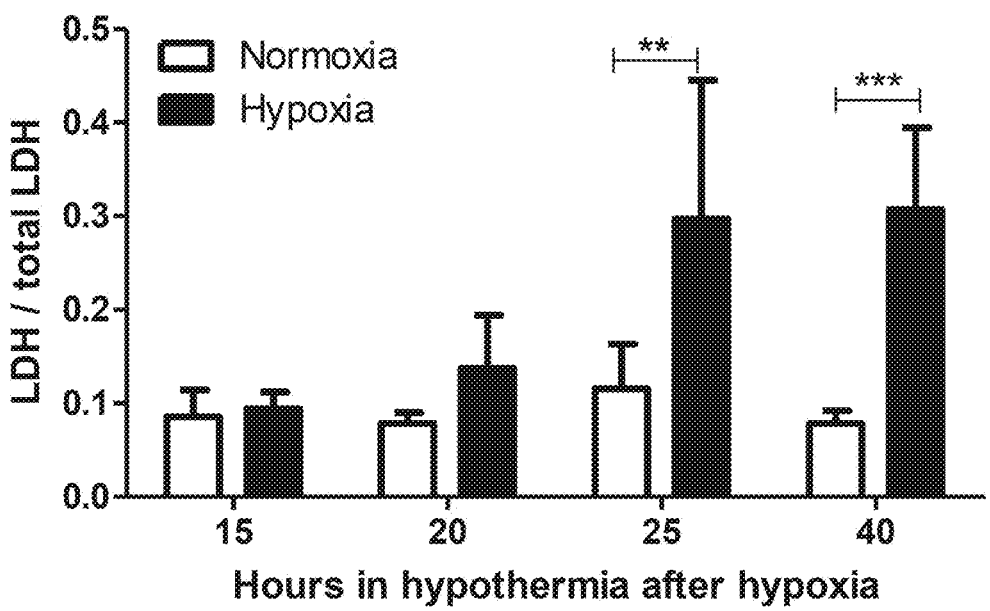
FIG. 6: Effect of duration of reperfusion phase in hypothermia after hypoxia on cell damage as expressed by LDH/total LDH. From 25 hours of reperfusion, a significant increase in cell damage was present.
Figure 7A:
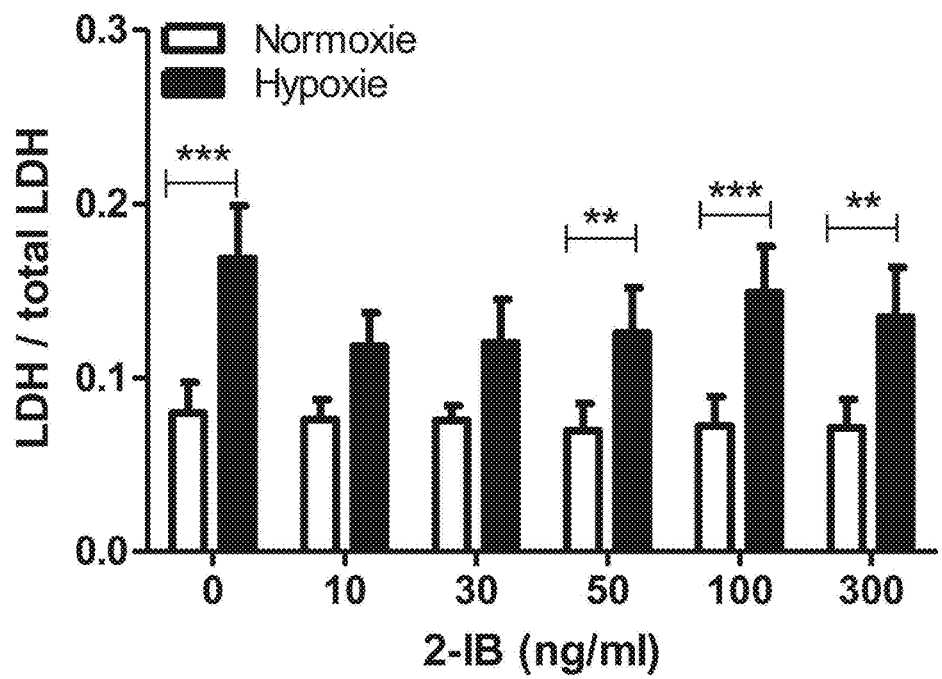
FIGS. 7A and 7B: Effects of 2-IB on hypoxia-induced cell damage during hypothermia. 2-IB attenuates hypoxia-induced cell damage. Columns display the mean; bars denote SD.
Figure 7B:
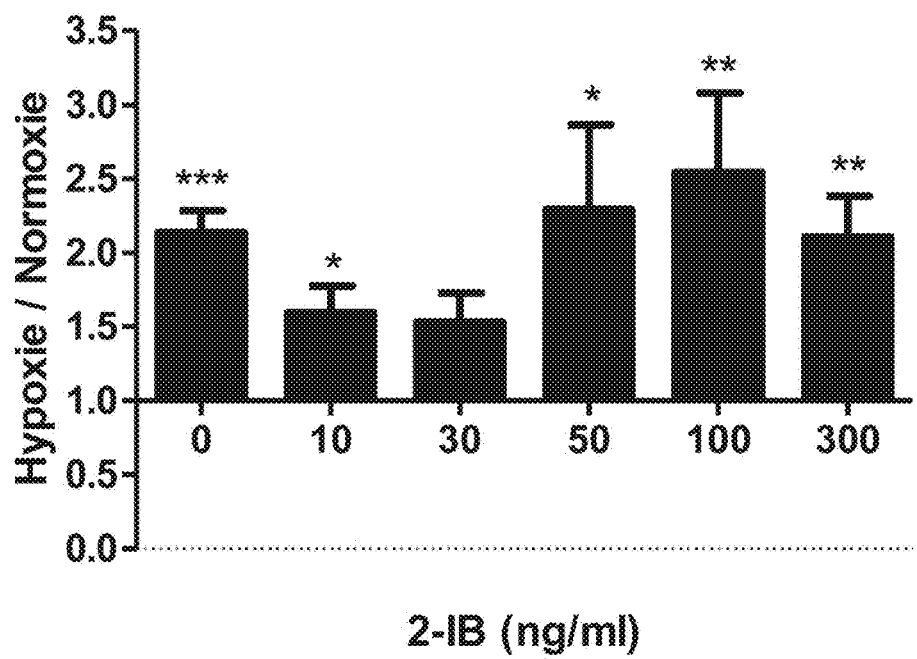
Figure 8A:
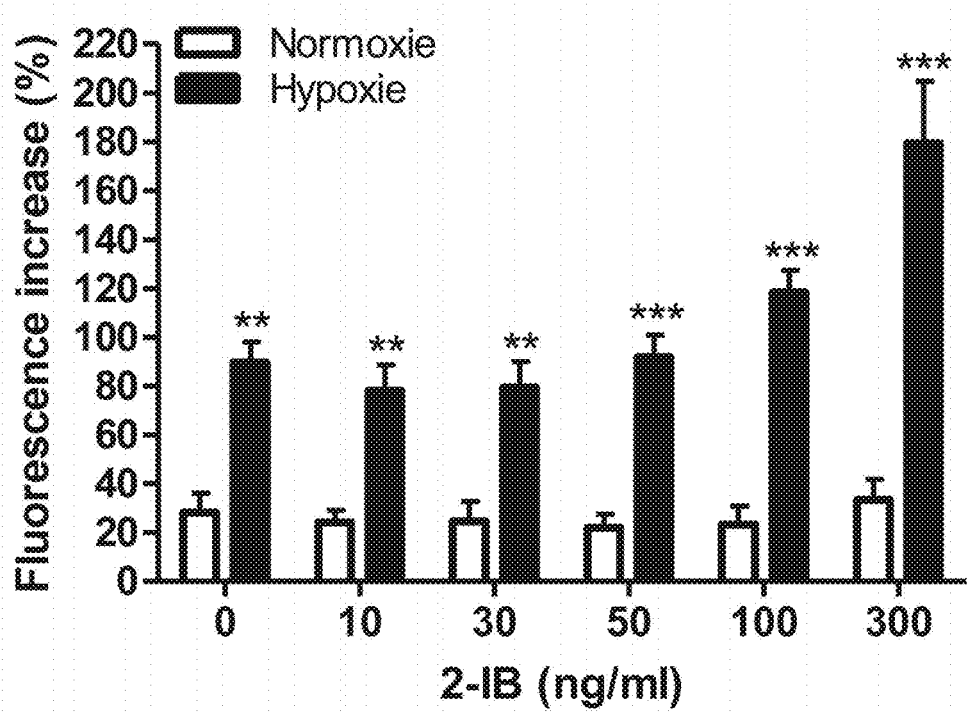
FIGS. 8A and 8B: Generation of hydrogen peroxide, expressed as increase in fluorescence (in %) for vehicle and all 2-IB doses during hypothermia. Columns display the mean; bars denote SD.
Figure 8B:
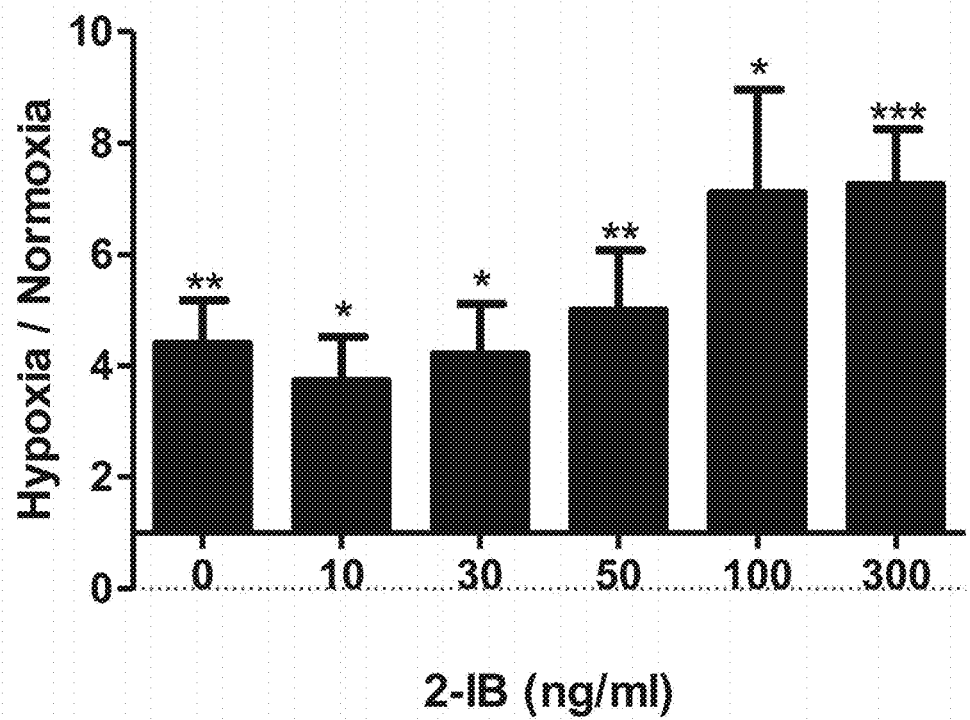
Figure 9:
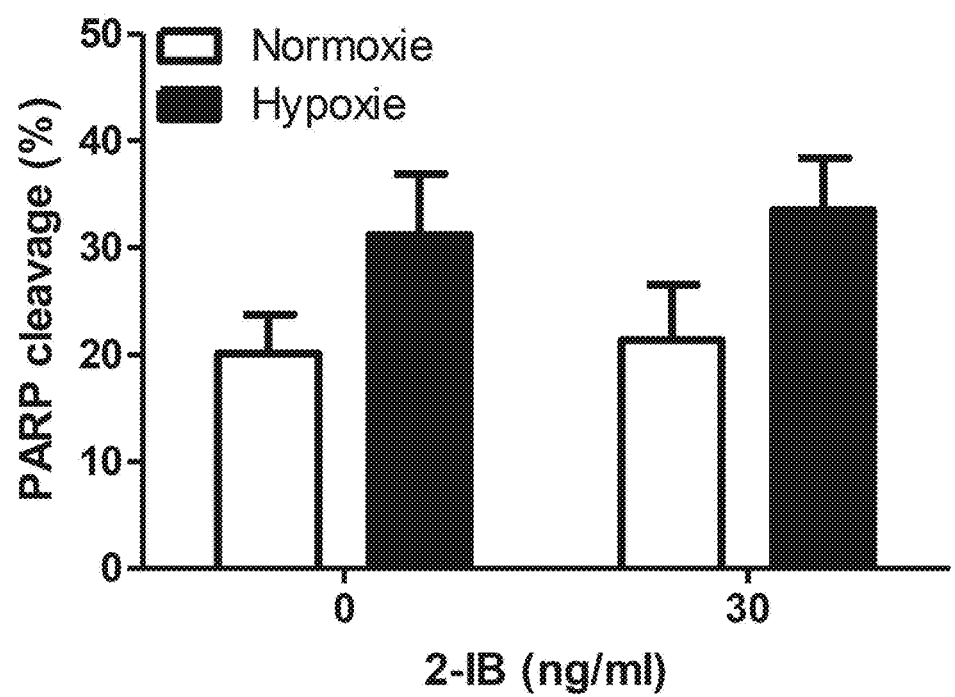
FIG. 9: PARP cleavage (in %) for vehicle and 2-IB (30 ng/ml) treatment during hypothermia. There was no significant increase in PARP cleavage after hypoxia.
Figure 10A:
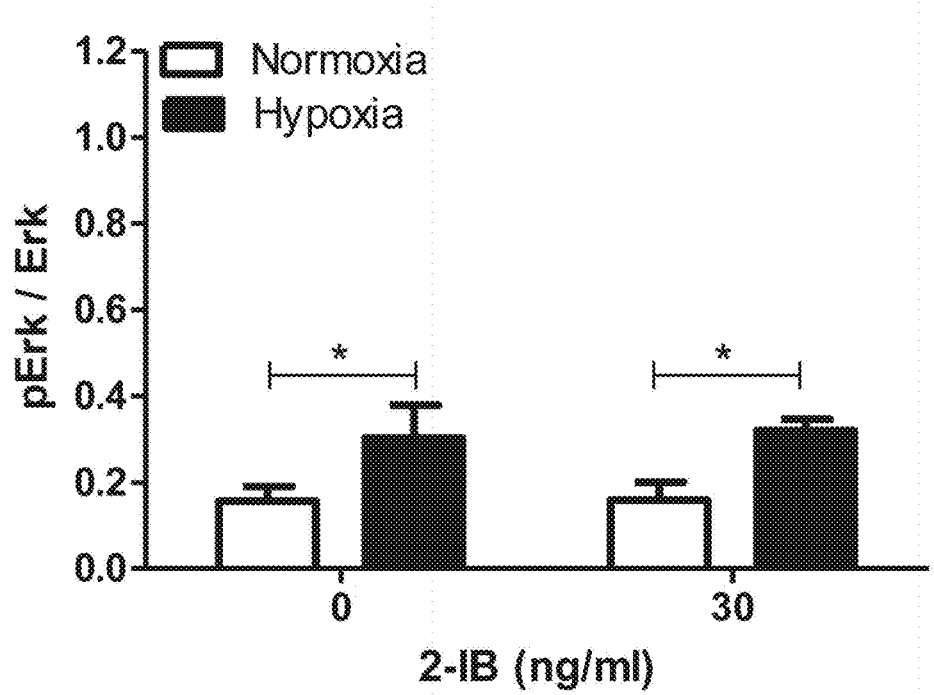
FIGS. 10A and 10B: Phosphorylation of Erk (FIG. 10A) and Akt (FIG. 10B) for vehicle and 2-IB (30 ng/ml) treatment during hypothermia. There was a significant increase in Erk phosphorylation after hypoxia, but not in Akt phosphorylation. Columns display the mean; bars denote SD. * $P<0.05$.
Figure 10B:
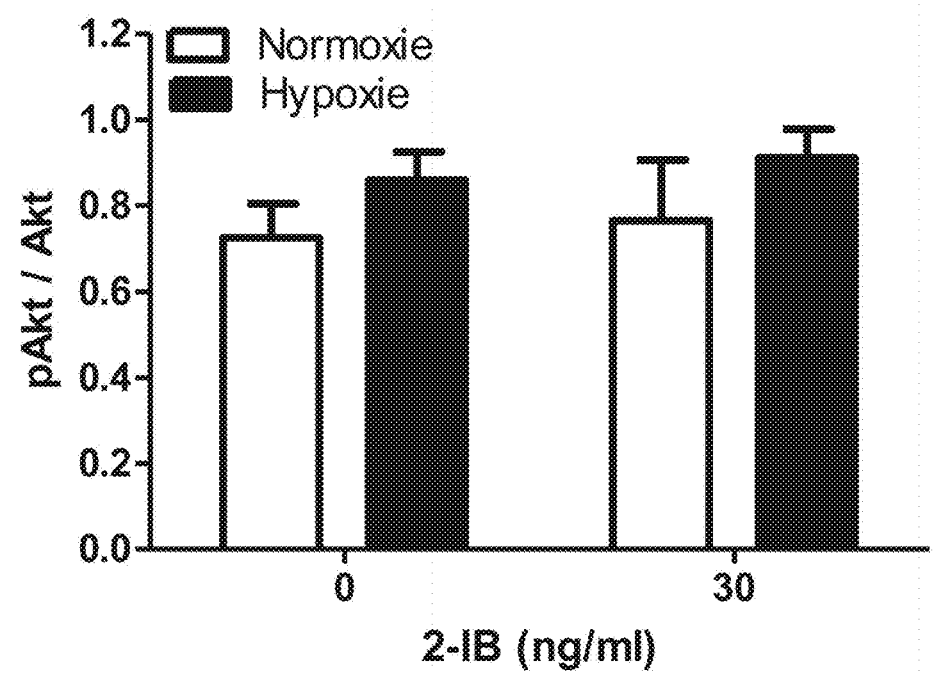

Results:

Hypoxia led to morphological signs of cell damage even under hypothermic conditions. Measurements of LDH as a marker of cell damage revealed a significant LDH increase earliest 25 hours after the hypoxic insult, if cell were grown under conditions of mild hypothermia ($p<0.01$), while under normothermic conditions comparable cell damage was already detectable as early as 17 hours after the hypoxic insult (FIG. 6). The post-hypoxic application of 30 ng/ml 2-IB reduced the hypoxia-induced LDH release even under hypothermia, resulting in LDH levels that were not statistically significant from values observed under normoxia (hypoxia: $p<0.01$ vs normoxia; hypoxia+2-IB: $p>0.05$ vs normoxia). FIGS. 7A, 7B) Post-hypoxic application of 2-IB (30 ng/ml) attenuated the hypoxia-induced ROS production under hypothermic conditions (hypoxia: $p<0.01$ vs normoxia; hypoxia+2-IB: $p<0.05$ vs normoxia). Higher concentrations of 2-IB were less effective in reducing hypoxia-induced ROS generation. Although culture medium concentrations of hydrogen peroxide were 9-fold increased by hypoxia under mild hypothermia ($p<0.001$ vs normoxia) post-hypoxic application of 2-IB did not influence generation of hydrogen peroxide. (FIGS. 8A and 8B) Cleavage of PARP and akt phosphorylation were by trend increased after the hypoxic insult (FIGS. 9 and 10B), while hypoxia significantly increased the phosphorylation of pro-survival erkl/2 ($p<0.05$ vs normoxia; FIG. 10A). Post-hypoxic addition of 2-IB under mild hypothermia did not influence cleavage or phosphorylation of the mentioned molecules (FIGS. 9, 10A and 10B).

Conclusion:

2-IB reduces hypoxia-induced neuronal cell damage under conditions of mild hypothermia. Combining 2-iminobiotin and mild hypothermia is a promising strategy for reducing hypoxia-induced cell damage.

Example 3: 2-IB Efficacy Following Forebrain Ischemia in Adult Rats

The modified four-vessel (4VO) occlusion model in adult rats is a very effective model to study the consequences of transient but severe brain ischemia (Pulsinelli and Buchan, 1988). Therefore, the aim of this study was to investigate whether 2-IB, administered upon reperfusion, can improve cognitive function in a 4VO rat model, mimicking cardiac arrest in adults.

Methods:

Four-Vessel Occlusion Model:

The rats were anesthetized using ketamine (90 mg/kg) and xylazine sodium (10%), as described earlier (Meilin et al., 2014). The first cervical vertebrata was exposed and the vertebral arteries were permanently occluded by electrocauterization. The common carotid arteries were isolated through a ventral midline neck incision and lifted using a 4.0 silk suture ligature, placed around them.

Twenty-four hours post vertebral arterial occlusion, the animals were reanesthetized using isoflurane. The common carotid arteries were exposed and occluded using microaneurysm clips for 15 minutes. After removing the clips reperfusion occurred. The skin of the incision at the neck was sutured using 4-0 silk suture. During the operation animal's core temperature was monitored using a rectal probe (Model 400; YSI Inc., Yellow Springs, Ohio, USA) connected to a thermometer (Model 8402-00; Cole-Parmer Instrument Co. Ltd, London, UK). The ischemic insult was initiated when a rectal temperature of 37-38° C. was achieved, and this temperature was maintained throughout the procedure using a heating mattress.

Sham operated animals underwent the same procedures without the occlusion of the vertebral and carotid arteries. The animals were anesthetized. The vertebral arteries were exposed without occlusion. The skin was then sutured and the animals returned to their cages. On study day 1 the animals were re-anesthetized and the common carotid arteries exposed without occlusion. The skin is then sutured and the animas are returned to their cages.

The presence of global ischemia was verified by removing the anesthesia for few seconds during the ischemia. Animals that did not show a righting reflex were considered ischemic, and were included in the study. Animals that showed unusual behavior not characteristic of historical behavior in this model at 24 hours post ischemia were excluded from the study.

Treatment

Treatment was given s.c. directly upon reperfusion, at 12 hours and 24 hours after occlusion, a treatment regimen already demonstrated to be neuroprotective in a neonatal HI rat model in (Van der Tweel, 2005). During the acclimatization period rats were randomly assigned to experimental groups. The animals were subjected to 4VO per cage or one rat per cage was subjected to HI. Rats received either vehicle (normal saline at pH 3.8-4.0) or 2-IB (1.1 mg/kg, 3.3 mg/kg, 10 mg/kg and 30 mg/kg dissolved in 5 ml/kg normal saline at pH 3.8-4.0). Each dosing group was kept in separate cages to avoid cross-contamination by consuming stools during the study period. The experimental groups were as follows.

TABLE 2

| Group Code | Group Size | Treatment | Dose | Volume ml/kg | Dosing Regimen |
|---|---|---|---|---|---|
| 1 | N = 6 | Sham Operated | N/A | N/A | N/A |
| 2 | N = 20 | Vehicle | 0 mg/kg | 5 | Directly upon reperfusion, 12 hours and 24 hours post reperfusion. |
| 3 | N = 15 | 2-IB | 1.1 mg/kg | 5 | |
| 4 | N = 14 | 2-IB | 3.3 mg/kg | 5 | |
| 5 | N = 13 | 2-IB | 10 mg/kg | 5 | |
| 6 | N = 13 | 2-IB | 30 mg/kg | 5 | |

Morris Water Maze test

Tests were performed during day-time. Rats were introduced to a standardized 1.2 m-diameter pool filled with water for 120 seconds or until they located a platform hidden 1 cm below the water surface. Several visual cues were provided within the room in which the pool was located to allow rats to spatially navigate the water maze. Rats that located the hidden platform were allowed to remain on it for 10 seconds, and rats that failed to find the platform within 120 seconds were placed on the platform for 10 seconds. Rats were allowed two attempts to find the hidden platform, and this learning test was performed over a period of 4 days (days 28-31). The memory test was performed on the fifth day (day 32), at which time the hidden platform was removed, and rats were placed in the pool for a single 60-second trial. The amount of time that each rat spent in the quadrant, where the hidden platform had previously been located, was recorded by an observer who was blinded to the experimental groups.

The Morris water maze was used to evaluate how well the rats remembered the location of the hidden platform, and whether they had learned to navigate towards the appropriate quadrant. The time that the rat spent in the right quadrant was measured. This was considered the primary outcome.

During the learning test the time to find a hidden platform in the water was calculated. Also the area under the curve (AUC) of the subsequent learning tests was calculated. These parameters were considered secondary outcomes.

Histology

Rats were sacrificed at 33 days after the insult with an overdose of pentobarbital sodium (100 mg/kg i.p.). Histological analysis was performed in at least 9 rats for each group. The brains of the other 3 rats per group were snap frozen in liquid nitrogen and were stored for future analysis. The brain was perfused via the left ventricle with heparinised normal saline to remove the excess of blood from the brain. Afterwards the brain was perfused with 4% paraformaldehyde phosphate-buffered saline. The whole brain was removed and immersed in formaldehyde for at least another 72 hours. Brains were embedded in paraffin. Coronal sections (6 mm) were cut at approximately 3.3 mm from the bregma and stained with hematoxylin-eosin. Sections were scored in a blinded way for living neurons in the right and left part of the CA1 region of the hippocampus, the most damaged area in this model of global ischemia. This was also considered a secondary outcome parameter.

Statistical Analysis

Using a power of 80% and an alpha of 0.05 with an estimated difference in means±SD of 8±4, at least 13 rats per experimental group were needed. However, a higher number of rats started the surgical procedure but were lost due to the surgical procedure. Sham-operated rats (n=6) only underwent the surgical procedure but did not underwent (permanent and temporary) vessel occlusion.

All data are expressed as mean±S.D. Statistical evaluation of the data was performed using one-way ANOVA when appropriate. For variables changes over time, general linear model analysis was used with baseline as co-variate. Post-hoc analysis was performed using Dunnett's two-sided test versus vehicle treatment. A p-value<0.05 was determined statistically significant. Statistical analysis was performed using SPSS (IBM, version 22).

Figure 11:
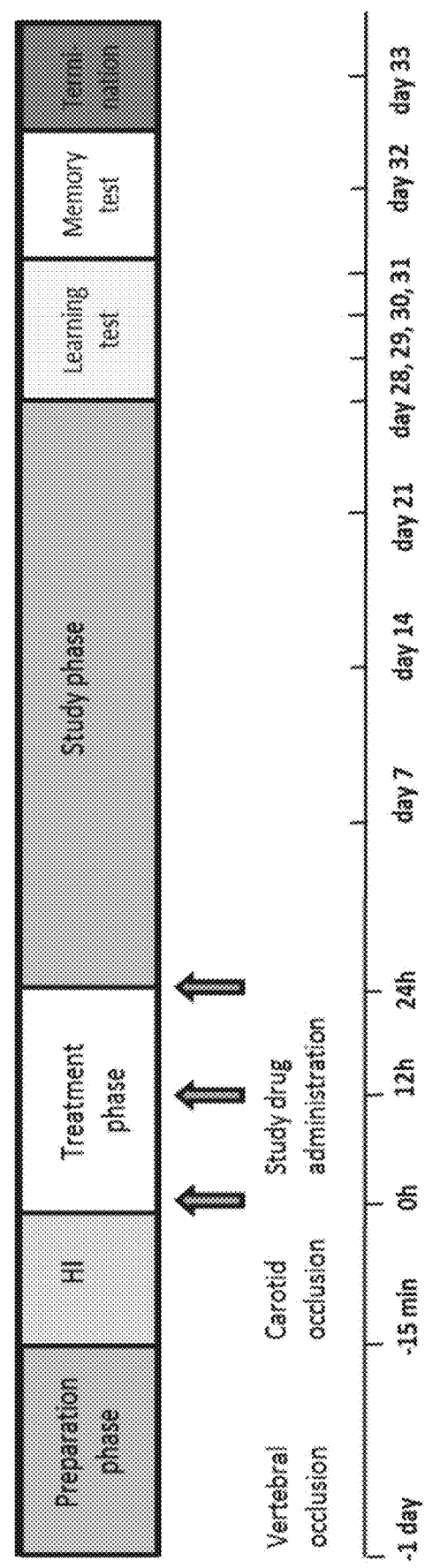
FIG. 11: Overview of study procedure in Example 3; HI=hypoxia-ischemia. Example 3.

See FIG. 11 for a schematic of the study procedure.

Results:

Animals

Bodyweight increased over time for all groups. There was no significant difference between treatment groups. Also no significant differences between blood glucose values were found.

Memory

Figure 12:
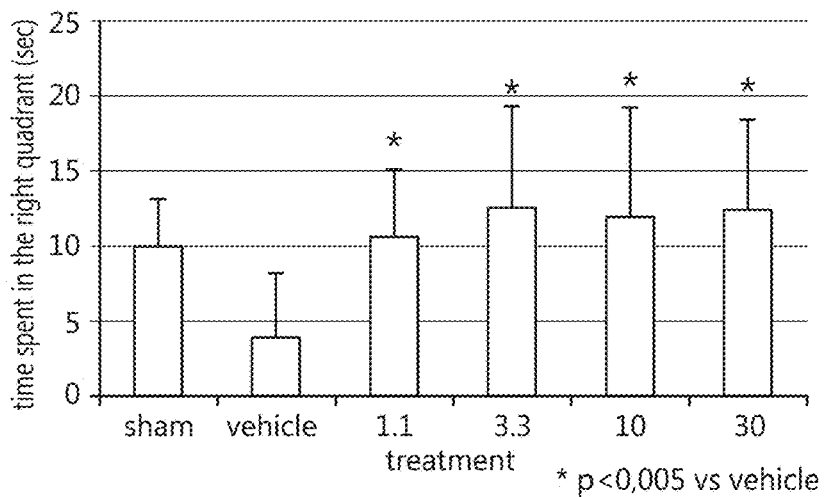
FIG. 12: Memory test (time spent in the right quadrant to find a hidden platform) at day 32 after 4VO for all treatment groups (mean±SD).

The memory test, defined as the time spent in the right quadrant on day 32, was 10.1±3.0 sec in sham-operated rats, 3.9±4.4 sec in the vehicle-treated rats, and 10.7±4.4, 12.7±6.7, 12.0±7.3, and 12.5±6.0 sec in the 1.1, 3.3, 10, and 30 mg/kg/dose 2-IB treated rats, respectively (FIG. 12). One-way ANOVA showed a significant difference between vehicle and 2-IB treatment groups (p<0.0005). Dunnett's post hoc analysis revealed a significant difference between vehicle and 1.1 mg/kg/dose (p=0.003), vehicle and 3.3 mg/kg/dose (p=0,000), vehicle and 10 mg/kg/dose (p=0.001), and vehicle and 30 mg/kg/dose group (p=0,000).

Learning Test

Figure 13:
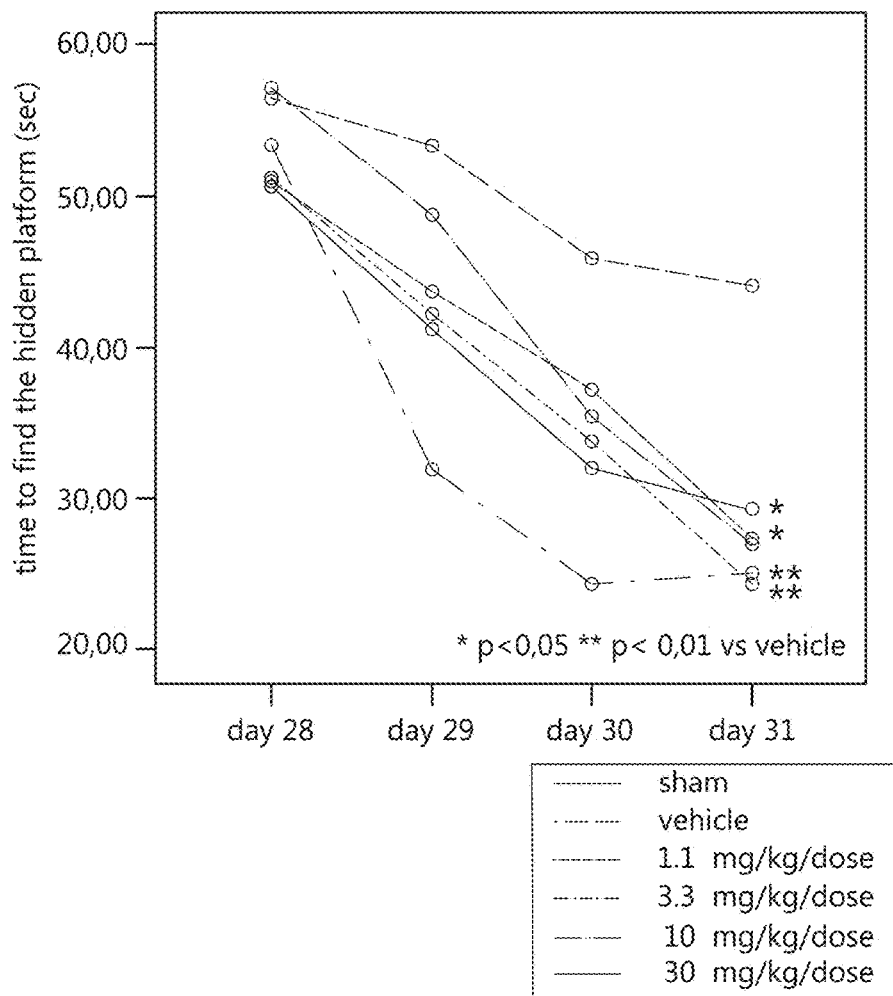
FIG. 13: Learning test from day 28 until day 31 after 4VO: time to find the hidden platform per treatment group.

Results from the learning test from day 28 to day 31 are shown in FIG. 13. General Linear Modelling showed a significant difference between treatment groups (p=0.004). Dunnett's post hoc analysis showed a significant difference between the sham (p<0.01), the 1.1 mg/kg/dose (p<0.05), the 3.3 mg/kg/dose (p<0.01), and the 30 mg/kg/dose (p<0.05) and the vehicle-treated rats.

The AUC of the learning test from day 28 until 31 was 231±84 in sham rats, 349±76 in vehicle-treated rats, 276±85, 266±64, 297±79, 287±89 in the 1.1, 3.3, 10, and 30 mg/kg/dose 2-IB treated rats, respectively. One way ANOVA showed a significant difference between groups (p<0.012). Dunnett's post hoc analysis revealed a significant difference between vehicle and 1.1 mg/kg/dose, and the vehicle and 3.3 mg/kg/dose group (p<0.05).

Histology

There was a significant decrease in surviving cells in the CA1 region caused by the 4VO (one-way-ANOVA p<0.005, post hoc analysis sham versus all other treatment p<0.005). Histology results showed 175±53 surviving cells in the CA1 region of the sham-operated rats, 39±51 in the vehicle-treated rats, and 29±34, 71±61, 63±54, and 50±51 in the 1.1, 3.3, 10, and 30 mg/kg/dose 2-IB treated rats, respectively. In the present study we studied the potential neuroprotective effects of 2-IB, a biotin analogue, on memory in a 4VO model using the Morris Water Maze test. 2-IB, administered in a dose range of 1.1 to 30 mg/kg/dose upon reperfusion, showed a significantly improved memory at 32 days after global ischemia. Furthermore, the learning curve to find a visible platform was significantly better in the 2-IB treated rats in a dose range of 1.1 to 30 mg/kg/dose compared to the vehicle treated rats, although no significant preserved amount of neuronal cells were seen in the CA1 area of the hippocampus at 33 days after 4VO.

In survivors of OHCA between 30% and 50% experience cognitive deficits for up to several years post-discharge (Green et al., 2015). Neuropsychological tests showed frequent impairments most often in the memory domain (Orbo et al., 2015). Even in patients that left the hospital with a CPC score of 1, reduced accuracy of working memory and speed of spatial memory was observed when a neurocognitive test battery was performed (Iannacone et al., 2014). The Morris Water Maze is a relatively simple procedure in which both the spatial memory (hidden-platform) and the non-spatial (visible platform) conditions of the memory are being tested (Bromley-Brits et al., 2011). The administration of 2-IB upon reperfusion after the 4VO, significantly increased the memory function of the rats to a degree comparable to the sham situation.

Memory deficits correspond pathophysiologically with neuronal damage mainly in the hippocampus (Bjorklundt et al., 2014). The 4VO model predominately leads to memory dysfunction based on neuronal injury in the CA1 region of the hippocampus (Pulsinelli and Buchan, 1988). After clinically relevant survival times, a spontaneous repopulation occurred in the CA1 region, but this was not sufficient to offset the behavioral impairments arising from the ischemic insult (Langdon et al., 2008). In the present study there was a significant decrease in surviving cells in the CA1 region of the hippocampus after HI. Treatment with 2-IB, however, did not show a significant difference versus vehicle, although there was a trend to an increased survival in a dose range of 3.3-30 mg/kg. All rats were sacrificed at 33 days after the HI insult. No rats were sacrificed at earlier time points, so we do not know whether repopulation in the hippocampus occurred already. We do know however, that with less surviving cells the memory function in the 2-IB treated rats was better than in vehicle treated rats.

Conclusion:

Adult rats treated s.c. with 3 gifts of 2-IB in a dose range of 1.1-30 mg/kg/dose directly upon reperfusion every 12 hours showed a significant improved memory after 4VO compared to vehicle-treated rats. At this moment a Phase 2 clinical trial has started to evaluate safety and pharmacokinetics in adults after OHCA.

REFERENCES

Block F., Schwarz M. Correlation between hippocampal neuronal damage and spatial learning deficit due to global ischemia. Pharmacology, biochemistry, and behavior. 1997 April; 56(4):755-61.

Björklund E., Lindberg E., Rundgren M., Cronberg T., Friberg H., Englund E. Ischaemic brain damage after cardiac arrest and induced hypothermia—a systematic description of selective eosinophilic neuronal death. A neuropathologic study of 23 patients. Resuscitation. 2014 April; 85(4):527-32.

Bjorkman S. T., Ireland Z., Fan X., van der Wal W. M., Roes K. C., Colditz P. B., Peeters-Scholte C. M. Short-term dose-response characteristics of 2-iminobiotin immediately post-insult in the neonatal piglet after hypoxia-ischemia. Stroke. 2013 March; 44(3):809-11.

Bromley-Brits K., Deng Y., Song W. Morris Water Maze Test for Learning and Memory Deficits in Alzheimer's Disease Model Mice. Journal of Visualized Experiments: JoVE. 2011; (53):2920. doi:10.3791/2920.

Buanes E. A., Gramstad A., Sovig K. K., Hufthammer K. O., Flaatten H., Husby T., Langorgen J., Heltne J. K. Cognitive function and health-related quality of life four years after cardiac arrest. Resuscitation. 2015 April; 89:13-8.

Ewy G. A., Bobrow B. J., Chikani V., Sanders A. B., Otto C. W., Spaite D. W., Kern K. B. The time dependent association of adrenaline administration and survival from out-of-hospital cardiac arrest. Resuscitation. 2015 November; 96:180-5.

Green C. R., Botha J. A., Tiruvoipati R. Cognitive function, quality of life and mental health in survivors of our-of-hospital cardiac arrest: a review. Anaesth. Intensive Care. 2015 September; 43(5):568-76.

Grupke S., Hall J., Dobbs M., Bix G. J., Fraser J. F. Understanding history, and not repeating it. Neuroprotection for acute ischemic stroke: from review to preview. Clin. Neurol. Neurosurg. 2015 February; 129:1-9.

Hasan O. F., Al Suwaidi J., Omer A. A., Ghadban W., Alkilani H., Gehani A., Salam A. M. The influence of female gender on cardiac arrest outcomes: a systematic review of the literature. Curr. Med. Res. Opin. 2014 November; 30(11):2169-78.

Heron M. Deaths: Leading Causes for 2012. National Vital Statistics Reports NVSS. 2015 August; 64(10):1-94.

Iannacone S., Leary M., Esposito E. C., Ruparel K., Savitt A., Mott A., Richard J. A., Gur R. C., Abella B. S. Feasibility of cognitive functional assessment in cardiac arrest survivors using an abbreviated laptop-based neurocognitive battery. Ther. Hypothermia Temp. Manag. 2014 September; 4(3):131-6.

Iqbal M. B., Al-Hussaini A., Rosser G., Salehi S., Phylactou M., Rajakulasingham R., Patel J., Elliott K., Mohan P., Green R., Whitbread M., Smith R., Ilsley C. Predictors of survival and favorable functional outcomes after an outof-hospital cardiac arrest in patients systematically brought to a dedicated heart attack center (from the Harefield Cardiac Arrest Study). Am. J. Cardiol. 2015 Mar. 15; 115(6):730-7.

Langdon K. D., Granter-Button S., Corbett D. Persistent behavioral impairments and neuroinflammation following global ischemia in the rat. Eur. J. Neurosci. 2008 December; 28(11):2310-8.

Lilja G., Nielsen N., Friberg H., Horn J., Kjaergaard J., Nilsson F., Pellis T., Wetterslev J., Wise M. P., Bosch F., Bro-Jeppesen J., Brunetti I., Buratti A. F., Hassager, C., Hofgren C., Insorsi A., Kuiper M., Martini A., Palmer N., Rundgren M., Rylander C., van der Veen A., Wanscher M, Watkins H., Cronberg T. Cognitive function in survivors of out-of-hospital cardiac arrest after target temperature management at 33° C. versus 36° C. Circulation. 2015 Apr. 14; 131(15):1340-9.

Mauri R., Burkart R., Benvenuti C., Caputo M. L., Moccetti T., Del Bufalo A., Gallino A., Casso C., Anselmi L., Cassina T., Klersy C., Auricchio A. Better management of out-of-hospital cardiac arrest increases survival rate and improves neurological outcome in the Swiss Canton Ticino. Europace. 2015 Sep. 7.

Meilin S., Machicao F., Elmlinger M. Treatment with Actovegin improves spatial learning and memory in rats following transient forebrain ischaemia. J. Cell. Mol. Med. 2014 August; 18(8):1623-30.

Mosier J., Itty A., Sanders A., Mohler J., Wendel C., Poulsen J., Shellenberger J., Clark L., Bobrow B. Cardiocerebral resuscitation is associated with improved survival and neurologic outcome from out-of-hospital cardiac arrest in elders. Acad. Emerg. Med. 2010 March; 17(3):269-75.

Nijboer C. H., Kavelaars A., van Bel F., Heijnen C. J., Groenendaal F. Gender-dependent pathways of hypoxia-ischemia-induced cell death and neuroprotection in the immature P3 rat. Dev. Neurosci. 2007; 29(4-5):385-92.

Ørbo M., Aslaksen P. M., Larsby K., Schäfer C., Tande P. M., Vangberg T. R., Anke A. Relevance of cognition to health-related quality of life in good-outcome survivors of out-of-hospital cardiac arrest. J. Rehabil. Med. 2015 Oct. 5; 47(9):860-6.

Ordy J. M., Thomas G. J., Volpe B. T., Dunlap W P., Colombo P. M. An animal model of human-type memory loss based on aging, lesion, forebrain ischemia, and drug studies with the rat. Neurobiology of aging. 1988 September-December; 9(5-6):667-83.

Peeters-Scholte C., Koster J., Veldhuis W., van den Tweel E., Zhu C., Kops N., Blomgren K., Bär D., van Buul-Offers S., Hagberg H., Nicolay K., van Bel F., Groenendaal F. Neuroprotection by selective nitric oxide synthase inhibition at 24 hours after perinatal hypoxia-ischemia. Stroke. 2002 September; 33(9):2304-10.

Pulsinelli W. A., Buchan A. M. The four-vessel occlusion rat model: method for complete occlusion of vertebral arteries and control of collateral circulation. Stroke. 1988 July; 19 (7):913-4.

Shah K. S., Shah A. S., Bhopal R. Systematic review and meta-analysis of out-of-hospital cardiac arrest and race or ethnicity: black US populations fare worse. Eur. J. Prev. Cardiol. 2014 May; 21(5):619-38.

Sup S. J., Green B. G., Grant S. K. 2-Iminobiotin is an inhibitor of nitric oxide synthases. Biochem. Biophys. Res. Commun. 1994 Oct. 28; 204(2):962-8.

Volpe B. T., Davis H. P., Colombo P. J. Preoperative training modifies radial maze performance in rats with ischemic hippocampal injury. Stroke; a journal of cerebral circulation. 1989 December; 20(12):1700-6.

Wallin E., Larsson I. M., Rubertsson S., Kristofferzon M. L. Cardiac arrest and hypothermia treatment—function and life satisfaction among survivors in the first 6 months. Resuscitation. 2014 April; 85(4):538-43.

Warren S. A., Prince D. K., Huszti E., Rea T. D., Fitzpatrick A. L., Andrusiek D. L, Darling S., Morrison L. J., Vilke G. M., Nichol G.; ROC Investigators. Volume versus outcome: More emergency medical services personnel on-scene and increased survival after out-of-hospital cardiac arrest. Resuscitation. 2015 September; 94:40-8.

Weis S. N., Pettenuzzo L. F., Krolow R., Valentim L. M., Mota C. S., Dalmaz C., Wyse A. T., Netto C. A. Neonatal hypoxia-ischemia induces sex-related changes in rat brain mitochondria. Mitochondrion. 2012 March; 12(2):271-9.

Example 4: Calculation of Dose in Human

The toxicokinetics of 2-IB was studied over a 96-hour period by i.v. pulse infusions to adult rats. The purpose of this study was to generate toxicokinetic parameters (Cmax, tmax, AUC, t1/2) from 2-IB plasma concentrations in male and female rats after repeated i.v. infusion.

Animals received six 15-minute pulses of 6.6, 13.3 or 27.5 mg/kg 2-IB, in a 24-hour period (total daily dose of 40, 80 and 165 mg/kg, respectively) in Groups 2, 3 and 4 respectively, for four consecutive days, for a total of 23 infusions. Group 1 received vehicle only. Systemic exposure was monitored on day 0 and day 4. Blood sampling was conducted at 15 minutes and 0.5, 1 and 4 hours after the first infusion, and 15 minutes and 0.5, 1, 4, 8 and 24 hours following the last dose.

For male and female rats and for first and last pulse mean AUC 0-4-hour values were respectively 2310, 2530, 1750 and 1950 ng·h/mL after 6.6 mg/kg per pulse. Across sexes and first and last pulses the overall mean was about 2135 ng·h/mL.

In Example 3, the most beneficial pharmacological effects were observed after dose levels as low as 1.1 mg/kg and up to and including 3.3 mg/kg. However, effects were also seen at higher doses. Assuming linear PK, a mean AUC of about 356 ng·h/mL can be expected at the 1.1 mg/kg dose level and an AUC of about 1068 ng·h/mL at the 3.3 mg/kg dose level. From a translational perspective an exposure of about 356 ng·h/mL can be regarded as the minimally effective target level for adult humans. Exposures up to and including 1068 ng·h/mL are also considered effective as well as higher exposures.

The pharmacokinetics of 2-IB have been investigated in a Phase I clinical study in which the safety and tolerability of single and multiple doses of 2-IB pulse i.v. infusion in healthy male subjects were investigated. The study was a randomized, double-blind, placebo-controlled, dose escalation study with 3 groups of 6 healthy male subjects receiving a single i.v. infusion or pulsed i.v. infusions of 2-IB or placebo in 3 periods. Treatments were randomized such that each subject received 2 out of 3 foreseen dose levels of 2-IB and once placebo.

For subjects receiving 6 pulses of 0.6 mg/kg in a 24-hour period mean AUC 4 hours was 1170 ng·h/ml after the first infusion and 1441 ng·h/ml after the last infusion. So on average, mean AUC 0-4 hours was about 1305 ng·h/mL during the 24-hour dosing period. Assuming linear PK a pulse dose of 0.16 mg/kg is expected to provide an exposure (AUC 4 hours) that corresponds to about 356 ng·h/mL.

Example 5A: 2-IB Treatment in Adults after OHCA (Out of Hospital Cardiac Arrest) Intervention The first cohort of eight patients will receive 2-IB in a dose of 0.055 mg/kg/dose every 4 hours iv, 6 times in total (part A; i.e., 0.33 mg/kg/day). The second cohort of eight patients (cohort B, i.e., 0.99 mg/kg/day) will receive an anticipated dose of 0.165 mg/kg/dose and the third cohort of eight patients will receive an anticipated dose of 0.500 mg/kg/dose (cohort C, i.e., 3 mg/kg/day). The first dose will be given as soon as possible and within 6 hours after OHCA. Escalation to the next dose level will be done after pharmacokinetic analyses have performed and no relevant safety issues have been encountered. All patients will be treated with temperature targeted management aiming at 36° C.
Investigational Product/Treatment All patients will receive open label 2-IB, which will be provided in vials of 50 ml with an extractable volume of 40 ml. No placebo will be used.

2-IB is formulated as a 0.75 mg/ml isotonic, iso-osmotic, saline solution for injection with a low quantity of citric buffer (about 15 mmol/l) at pH 4.0. 2-IB will be administered intravenously through a percutaneously inserted central catheter to decrease the risk of extravasation of the acid solution using a dual or multiple lumen catheter. Study medication will be used undiluted and transferred to a syringe, the volume depends on the patient's weight.

Infusion times (15 minutes per dose) will be identical within and among groups A, B and C, and infusion rates will be adjusted (tripled) in Group B as compared to Group A by increasing the infusion rate. In Group C the doses and infusion rates will again be tripled as compared to Group B.

As an example, a patient of 80 kg in Group A will receive 0.055 mg/kg=0.055×80=4.4 mg 2-IB per dose, which is equivalent to 5.9 ml of injection fluid per dose.

Results

Patients in all three cohorts will be monitored as follows.

The levels of neuron specific enolase (NSE) and S100b at 24 and 48 hours after first dose of 2-IB will be determined. (See Rundgren Resuscitation. 2009 July; 80(7):784-9 and Shinozaki Crit. Care. 2009; 13(4):R121, for a description of determining levels of these markers and their use in predicting patient outcome.)

The CPC (Cerebral Performance Categories), CAMCI (Computerized Assessment for Mild Cognitive Injury) and short IQCODE (Informant Questionnaire on Cognitive Decline) scores will be recorded at 30 days after OHCA. (See Lilj a BMC Cardiovascular Disorders 2013, 13:85 and Sabedra Resuscitation 2015 90: 67-72 for description of cognitive function tests.)

Patients in all three cohorts may exhibit higher average cognitive scores as compared to historic controls of OHCA.

Example 5B: 2-IB Treatment in Adults after OHCA

Intervention:

A study was performed as described in Example 5A. Namely, a first cohort of eight patients received 2-IB in a dose of 0.055 mg/kg/dose every 4 hours iv, 6 times in total (part A; i.e., 0.33 mg/kg/day).

The eight adults that suffered an out of hospital cardiac arrest were treated with 2-IB as a 15-minute IV infusion every 4 hours for 6 administrations. Target temperature management was used to maintain body temperature of 36.0 (median). Based on the results for the first cohort, it was determined that the second and third cohort described in Example 5A were not necessary.

Analysis:

In all patients serum creatinine was determined at baseline (during admittance to hospital). eGFR (estimated glomerular filtration rate) was determined by using the following equation:

$$eGFR = 186 * SeCr^{-1.154} * Age^{-0.203} * 0.724^{SEX}$$

Sex: males=0; females=1.

(See for determining eGFR Rule AD, Larson T. S., Bergstralh E. J., Slezak J. M., Jacobsen S. J., Cosio F. G. Using serum creatinine to estimate glomerular filtration rate: accuracy in good health and in chronic kidney disease. Ann. Intern. Med. 2004 Dec. 21; 141(12):929-37).

Models were generated in order to determine the impact of dose adjustments and variability of AUC.

Results:

Patient characteristics are reported in Table 3.

TABLE 3

| ID | Dose (mg) | Age (years) | Body Weight (kg) | Sex | eGFR at T = 0 (mL/minute) | SeCre at T = 0 (μM) | Median Temp (° C.) |
|---|---|---|---|---|---|---|---|
| 1 | 3.6 | 47 | 65 | Male | 103 | 75 | 36.4 |
| 2 | 6.3 | 63 | 114 | Male | 87 | 82 | 36.1 |
| 3 | 4.7 | 60 | 85 | Male | 208 | 39 | 35.8 |
| 4 | 4.4 | 60 | 79 | Female | 87 | 64 | 36.0 |
| 5 | 6.9 | 74 | 125 | Male | 35 | 177 | 36.2 |
| 6 | 5.0 | 71 | 90 | Male | 48 | 136 | 35.8 |
| 7 | 4.7 | 61 | 85 | Male | 66 | 105 | 36.1 |
| 8 | 6.1 | 59 | 110 | Male | 56 | 122 | 35.8 |

Clearance appeared to increase with increasing eGFR or SeCre, no change seen for other covariates. Volume appeared to increase with body weight, no difference for other covariates.

The exposure metrics are shown in Table 4.

TABLE 4

| ID | CL (L/h) | V (L) | $V_{SS}$ (L) | AUCinf (ng · h/mL) | AUC cumul. (ng · h/mL) | thalf (h) |
|---|---|---|---|---|---|---|
| 1 | 11.4 | 5.0 | 15.0 | 315 | 1858 | 1.3 |
| 2 | 18.3 | 14.1 | 24.1 | 343 | 2032 | 1.2 |
| 3 | 22.3 | 19.0 | 28.9 | 209 | 1236 | 1.2 |
| 4 | 16.7 | 5.0 | 14.9 | 265 | 1577 | 1.0 |
| 5 | 6.4 | 24.3 | 34.3 | 1152 | 5613 | 3.9 |
| 6 | 5.8 | 11.3 | 21.3 | 860 | 4680 | 2.8 |
| 7 | 7.6 | 7.3 | 17.3 | 612 | 3521 | 1.9 |
| 8 | 4.9 | 33.6 | 43.5 | 1242 | 5386 | 6.3 |
| Mean | 11.7 | 14.9 | 24.9 | 625 | 3238 | 2.5 |
| StDev | 6.6 | 10.1 | 10.1 | 413 | 1794 | 1.8 |
| CV | 57 | 68 | 41 | 66 | 55 | 75 |
| Min | 4.9 | 5.0 | 14.9 | 209 | 1236 | 1.0 |
| Median | 9.5 | 12.7 | 22.7 | 478 | 2777 | 1.6 |
| Max | 22.3 | 33.6 | 43.5 | 1242 | 5613 | 6.3 |

As the drug is generally at steady-state within the dosing period, AUCinf has been used for simulations rather than AUC4. AUCinf=D.CL and can be easily derived. (D=dose; CL=clearance)

The parameter estimates vary slightly for the covariate model with Crea0 compared to the basic model. See Table 5.

TABLE 5

| ID | CL (L/h) | V (L) | $V_{SS}$ (L) | AUCinf (ng · h/mL) | AUC cumul. (ng · h/mL) | thalf (h) |
|---|---|---|---|---|---|---|
| 1 | 10.3 | 4.7 | 14.0 | 349 | 2063 | 1.3 |
| 2 | 17.9 | 14.5 | 23.8 | 352 | 2085 | 1.2 |
| 3 | 16.0 | 21.3 | 30.6 | 291 | 1694 | 1.5 |
| 4 | 16.3 | 5.1 | 14.4 | 271 | 1615 | 1.0 |
| 5 | 6.0 | 24.5 | 33.8 | 1235 | 5934 | 4.1 |

TABLE 5-continued

| ID | CL (L/h) | V (L) | $V_{SS}$ (L) | AUCinf (ng·h/mL) | AUC cumul. (ng·h/mL) | thalf (h) |
|---|---|---|---|---|---|---|
| 6 | 5.6 | 11.8 | 21.1 | 884 | 4803 | 2.8 |
| 7 | 10.0 | 7.2 | 16.5 | 464 | 2726 | 1.4 |
| 8 | 5.7 | 34.1 | 43.4 | 1063 | 4886 | 5.4 |
| Mean | 11.0 | 15.4 | 24.7 | 614 | 3226 | 2.3 |
| StDev | 5.1 | 10.5 | 10.5 | 386 | 1708 | 1.6 |
| CV | 47 | 68 | 42 | 63 | 53 | 69 |
| Min | 5.6 | 4.7 | 14.0 | 271 | 1615 | 1.0 |
| Median | 10.2 | 13.2 | 22.5 | 408 | 2405 | 1.5 |
| Max | 17.9 | 34.1 | 43.4 | 1235 | 5934 | 5.4 |

An exploratory covariate analysis was performed looking at body weight, age, eGFR, SeCre, and Core temperature. The model used was as follows:

$$Par_i = \theta_1 \left(\frac{Cov_i}{medianCov}\right)^{\theta_2} \cdot e^{\eta_i}$$

θ are parameters describing the relationship between PK parameter and covariates;
η describes the inter-individual variability.

The covariate analysis indicates that SeCre and temperature may have an influence on CL, and weight on volume.

Figure 14:
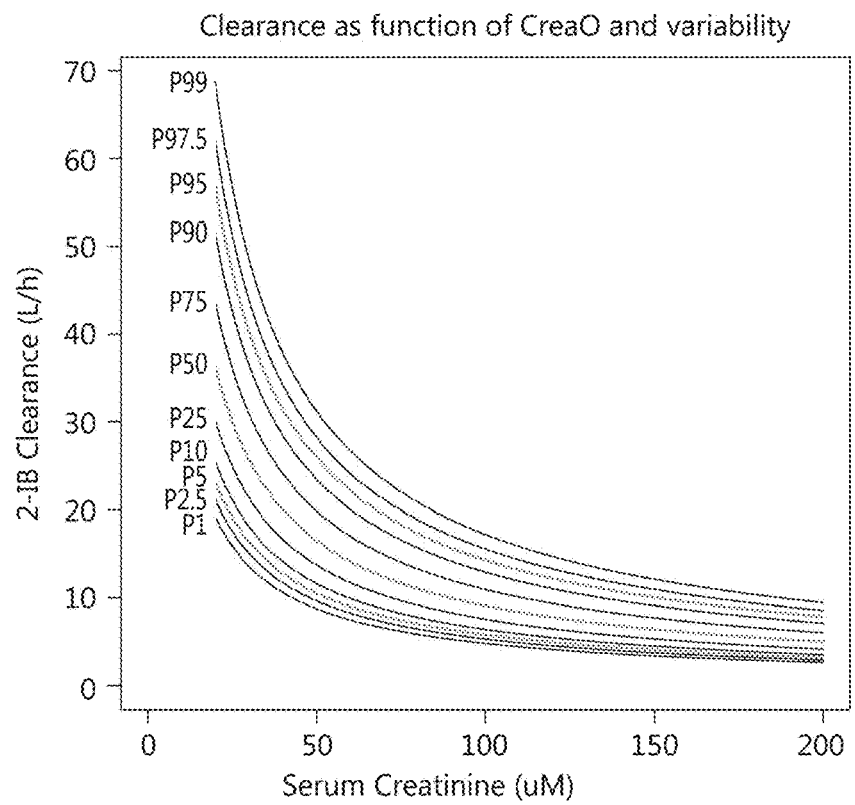
FIG. 14: Clearance and the dose required to reach the target vary as a function of SeCre (serum creatinine).
Figure 14:
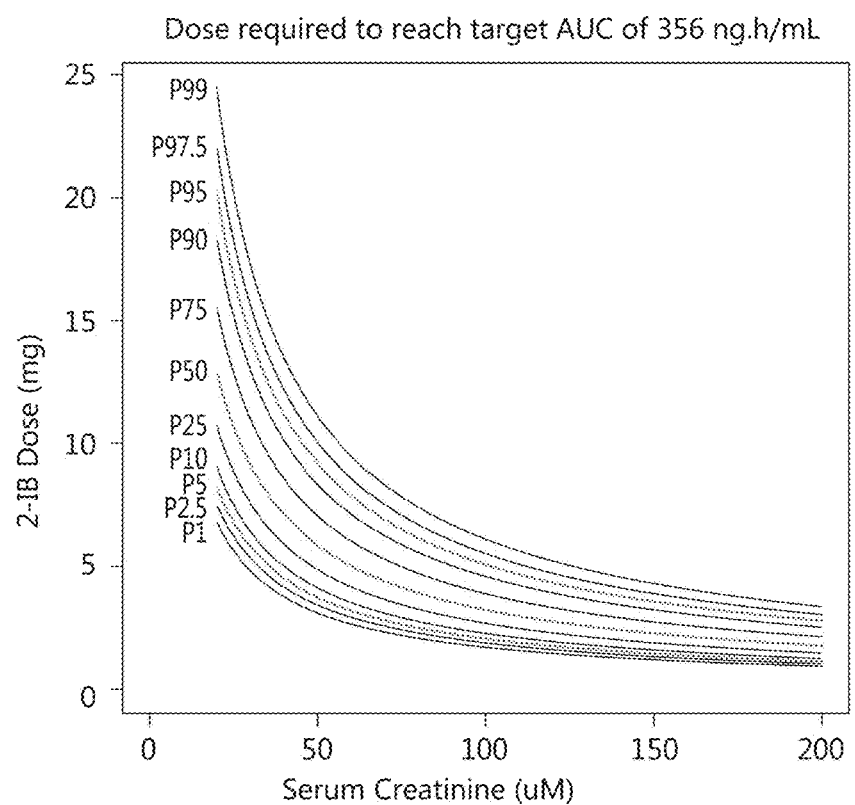

The variability in clearance is greatly reduced by taking SeCre levels into account. FIG. 14 demonstrates that clearance and the dose required to reach the target vary as a function of SeCre.

Figure 15A:
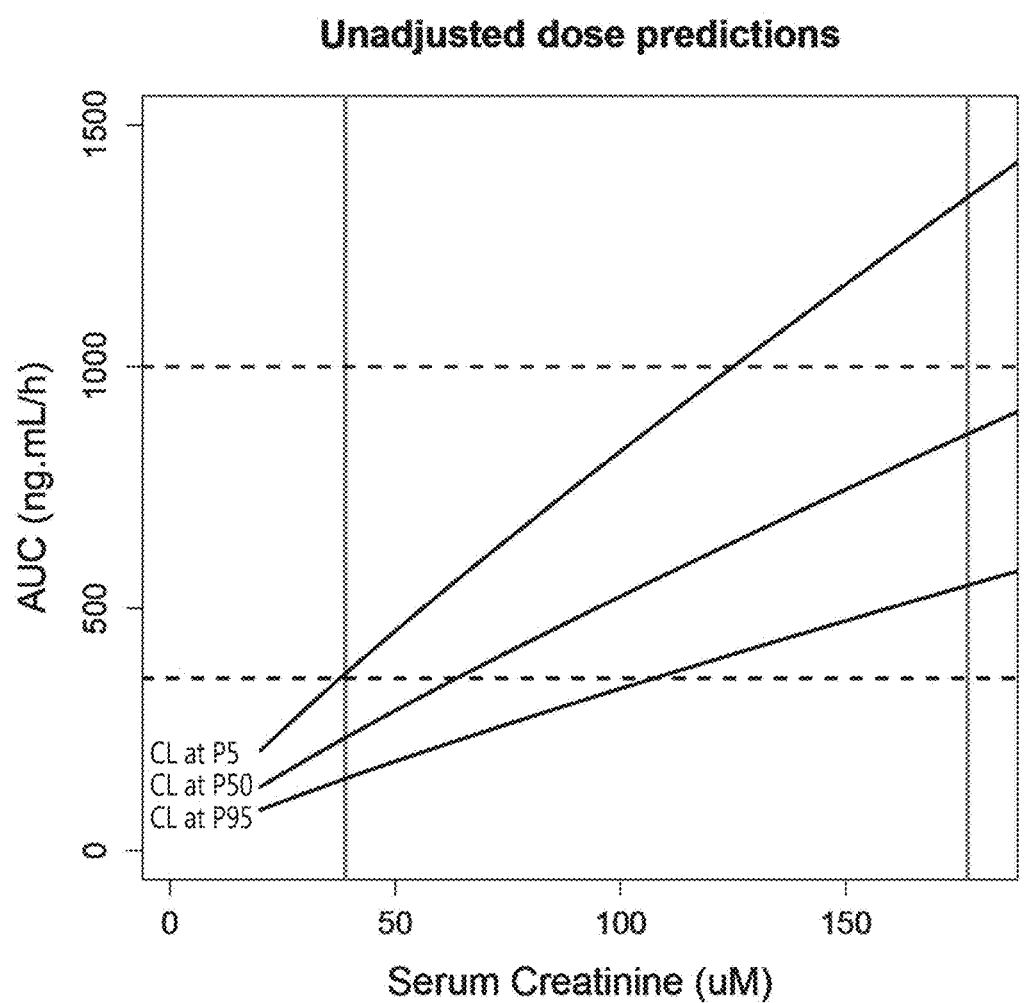
FIGS. 15A and 15B: Unadjusted and SeCre adjusted dose predictions. The dotted line indicates target exposure of 356 ng·mL/h, Crea0 range in grey. (Crea0 indicates serum creatinine at baseline).
Figure 15B:
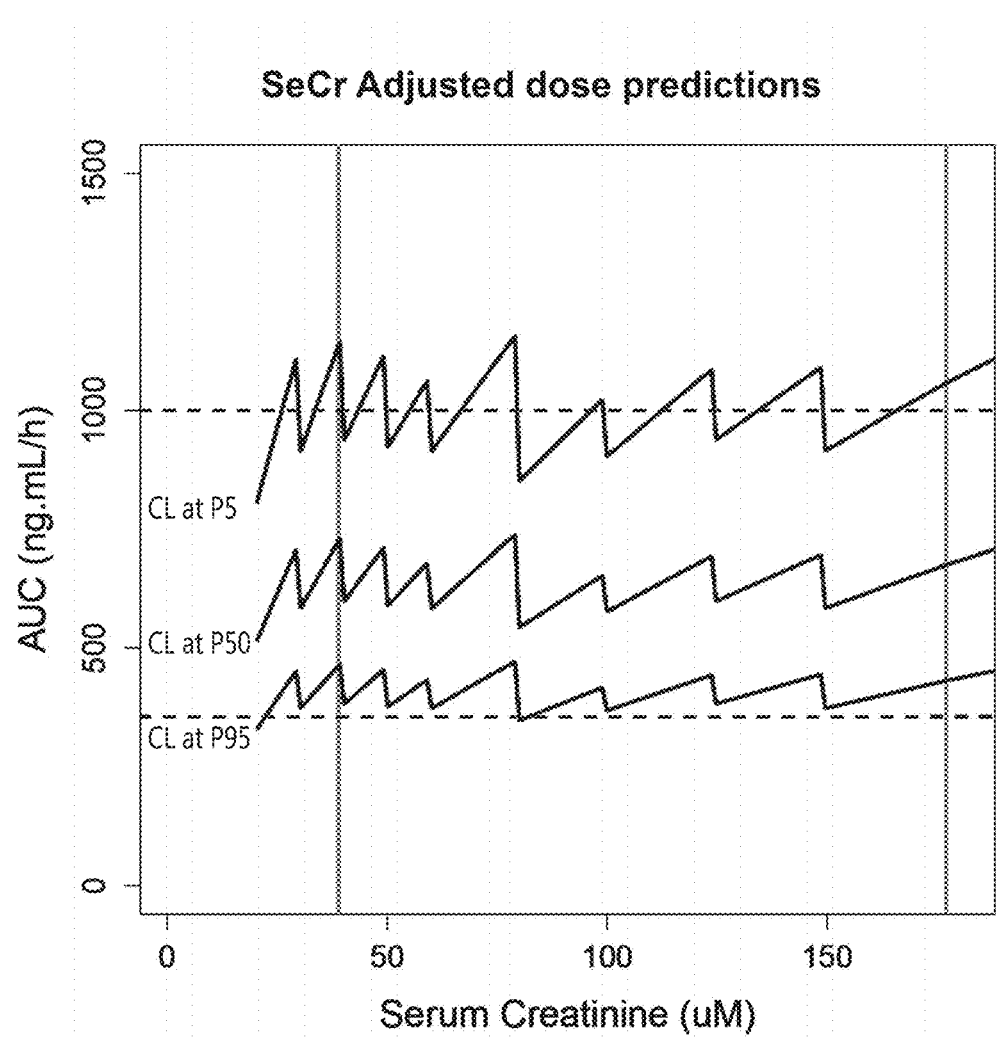

In a prediction model, adjusting dosages for Crea0 improves the ability of reaching the target AUC (see FIGS. 15A and 15B).

Table 6 depicts dosages for achieving an exposure of 356 ng·h/mL in 50% of patients (independent of weight).

TABLE 6

| SeCre (μM) before treatment | Dose (mg) |
|---|---|
| 20-30 | 15 |
| 30-40 | 10 |
| 40-50 | 7.5 |
| 40-75 | 6 |
| 75-100 | 4 |
| 100-150 | 3 |
| 150-200 | 2 |

Table 7 depicts dosages for achieving an exposure of 356 ng·h/mL in 95% of patients (independent of weight).

TABLE 7

| Serum Creatinine (μM) | | Dose volume (mL) | Dose (mg) |
|---|---|---|---|
| low | high | | |
| 20 | <30 | 25 | 18.75 |
| 30 | <40 | 20 | 15.00 |
| 40 | <50 | 16 | 12.00 |
| 50 | <60 | 13 | 9.75 |
| 60 | <80 | 11 | 8.25 |
| 80 | <100 | 8 | 6.00 |
| 100 | <125 | 7 | 5.25 |
| 125 | <150 | 6 | 4.50 |
| 150 | <200 | 5 | 3.75 |

Table 8 depicts a comparison of the AUC values obtained with the covariate model with Crea0 and the dose predictions, as well a flat dosing.

TABLE 8

| ID | Serum Creatinine (μM) | WT (kg) | Obs. AUCinf (based on weight) | Sim. AUCinf when dosing based on Crea0 from Table 6 | Sim. AUCinf when dosing based on 4.8 mg for all |
|---|---|---|---|---|---|
| 1 | 75 | 65 | 349 | 722 | 427 |
| 2 | 82 | 114 | 352 | 327 | 266 |
| 3 | 39 | 85 | 291 | 676 | 220 |
| 4 | 64 | 79 | 271 | 494 | 292 |
| 5 | 177 | 125 | 1235 | 588 | 765 |
| 6 | 136 | 90 | 884 | 781 | 847 |
| 7 | 105 | 85 | 464 | 692 | 642 |
| 8 | 122 | 110 | 1063 | 1070 | 993 |

The variability in clearance is also greatly reduced when taking eGFR levels into account.

Table 9 depicts a comparison of the AUC values obtained with the covariate model and the eGFR0 (eGFR taken at baseline) model.

TABLE 9

| ID | CL (L/h) | V (L) | $V_{SS}$ (L) | AUCinf (ng·h/mL) | AUC (ng·h/mL) | thalf (h) |
|---|---|---|---|---|---|---|
| 1 | 10.3 | 4.7 | 14.0 | 349 | 2060 | 1.3 |
| 2 | 18.1 | 14.8 | 24.1 | 348 | 2061 | 1.2 |
| 3 | 15.9 | 21.1 | 30.4 | 292 | 1705 | 1.5 |
| 4 | 16.1 | 5.0 | 14.3 | 274 | 1636 | 1.0 |
| 5 | 6.0 | 24.5 | 33.8 | 1227 | 5905 | 4.1 |
| 6 | 5.6 | 11.8 | 21.1 | 886 | 4813 | 2.8 |
| 7 | 10.1 | 7.3 | 16.5 | 462 | 2712 | 1.4 |
| 8 | 5.7 | 34.2 | 43.5 | 1067 | 4896 | 5.4 |
| Mean | 11.0 | 15.4 | 24.7 | 613 | 3224 | 2.3 |
| StDev | 5.1 | 10.5 | 10.5 | 385 | 1703 | 1.6 |
| CV | 47 | 68 | 42 | 63 | 53 | 69 |
| Min | 5.6 | 4.7 | 14.0 | 274 | 1636 | 1.0 |
| Median | 10.2 | 13.3 | 22.6 | 405 | 2387 | 1.5 |
| Max | 18.1 | 34.2 | 43.5 | 1227 | 5905 | 5.4 |

Table 10 depicts a comparison of the AUC values obtained with the covariate model with eGFR and the dose predictions, as well a flat dosing.

TABLE 10

| ID | eGFR (μM) | WT (kg) | Obs. AUCinf (based on weight) | Sim. AUCinf when dosing based on eGFR | Sim. AUCinf when dosing based on 4.8 mg for all |
|---|---|---|---|---|---|
| 1 | 103 | 65 | 349 | 800 | 472 |
| 2 | 87 | 114 | 348 | 415 | 269 |
| 3 | 208 | 85 | 292 | 802 | 306 |
| 4 | 87 | 79 | 274 | 465 | 302 |
| 5 | 35 | 125 | 1227 | 626 | 814 |
| 6 | 48 | 90 | 886 | 806 | 873 |
| 7 | 66 | 85 | 462 | 596 | 484 |
| 8 | 56 | 110 | 1067 | 922 | 856 |
| Mean | 86 | 94 | 613 | 679 | 547 |
| StDev | 54 | 20 | 385 | 181 | 261 |
| CV | 63 | 21 | 63 | 27 | 48 |
| Min | 35 | 65 | 274 | 415 | 269 |
| Median | 77 | 88 | 405 | 713 | 478 |
| Max | 208 | 125 | 1227 | 922 | 873 |

Table 10 demonstrates that there is a substantial decrease in the variability in exposure when the dosage is adjusted based on eGFR.

Based on the exploratory covariate analysis, we conclude that:
- Clearance appears to be influenced be renal function, here expressed as Serum Creatinine or eGFR based on serum creatinine before treatment, as well as body temperature
- Volume is influenced by body weight, which has no effect on the exposure in this study.
- Clearance is not influenced by body weight.

Accordingly, dosing based on serum creatinine or eGFR instead of a weight adjusted dosage, can be administered to patients in order to consistently achieve the desired exposure level.

Example 5C: 2-IB Treatment in Adults after OHCA Under Hypothermia

A study performed will be performed in four to six adults after out of hospital cardiac arrest treated with 2-IB as a 15-minute IV infusion every 6 hours for 4 administrations under 33 degrees Celsius hypothermia.

Based on the results from Example 5B, the 2-IB dosage needed to reach target exposure can be determined as follows:

Dose correction for use at lower temperatures can be determined using the following equation:

$$CL = 9.80 * \left(\frac{T}{36}\right)^{11.5} * \left(\frac{Crea0}{93.5}\right)^{-0.947}$$

This means that given the same Crea0, this would suggest CL could decrease to 37% of the CL at 36° when temperature is 33°. To achieve the same AUC the dose should be decreased to 37% of the original dose. Furthermore, the time interval to the next dose should be increased to about 6 hours.

What is claimed is:

1. A method for treating brain hypoxic injury under conditions of stroke in an individual, the method comprising administering to an individual in need thereof a therapeutically effective amount of 2-iminobiotin, such that after the first dose, the area under the plasma concentration time curve from 0 to 4 hours (AUC 0-4h) for 2-iminobiotin is at least 100 ng·h/mL,
wherein the individual is not a neonate.

2. The method according to claim 1, wherein the AUC 0-4h is at least 356 ng·h/mL.

3. The method according to claim 1, wherein the AUC 0-4h is between 300 ng·h/mL to 2000 ng·h/mL.

4. The method according to claim 1, wherein 2-iminobiotin is administered to the individual prior to surgery.

5. The method according to claim 1, wherein 2-iminobiotin is administered to the individual 1-5 hours prior to surgery.

6. The method according to claim 1, wherein the method is for prophylactically treating reperfusion injury after stroke in an individual.

7. The method according to claim 6, wherein the individual is at risk of reperfusion injury as a result of surgery.

8. A method for treating brain hypoxic injury under conditions of stroke in an individual, the method comprising administering to an individual in need thereof a therapeutically effective amount of 2-iminobiotin, wherein the individual is not a neonate and wherein the method comprises administering to the individual:
   a) 0.01 to 10 mg/kg/day of 2-iminobiotin, wherein the 2-iminobiotin is administered essentially continuously or every four to six hours per day;
   b) 6-120 mg/day of 2-iminobiotin, wherein the 2-iminobiotin is administered essentially continuously or provided in at least three doses per day;
   c) 0.01 to 5 mg/kg/day of 2-iminobiotin, wherein the 2-iminobiotin is administered essentially continuously or provided every four to six hours per day, and wherein the treatment is combined with hypothermia; or
   d) 4-20 mg/day of 2-iminobiotin, wherein the 2-iminobiotin is administered essentially continuously or provided in at least three doses per day, and wherein the treatment is combined with hypothermia.

9. The method according to claim 8, wherein 2-iminobiotin is administered such that the area under the plasma concentration time curve from 0 to 4 hours (AUC 0-4h) is between 100·h/mL to 2000·h/mL.

10. The method according to claim 8, wherein 2-iminobiotin is administered to the individual prior to surgery.

11. The method according to claim 10, wherein the 2-iminobiotin dose is to the individual 1-5 hours prior to surgery.

12. The method according to claim 8, wherein stroke is cerebral ischemic stroke.

13. The method according to claim 1, wherein the individual is a human of at least one year of age.

14. The method according to claim 8, wherein the 2-iminobiotin is administered intravenous, intraarterial, intrathecal, subdural, subarachnoidal, subcapsular, subarachnoid, and/or intraspinal.

15. The method according to claim 1, wherein stroke is cerebral ischemic stroke.

16. The method according to claim 8, wherein the method is for prophylactically treating reperfusion injury after stroke in an individual.

17. The method according to claim 16, wherein the individual is at risk of the reperfusion injury as a result of surgery.

18. A method for treating brain hypoxic injury under conditions of stroke in an individual, the method comprising
determining the serum creatinine concentration and/or estimated glomerular filtration rate (eGFR) in the individual and
administering one or more doses of 2-iminobiotin, wherein the dose of 2-iminobiotin is adjusted based on the individual's serum creatinine concentration and/or estimated glomerular filtration rate (eGFR).

19. The method according to claim 18, wherein the method is for prophylactically treating reperfusion injury after stroke in an individual.

20. The method according to claim 1, wherein the 2-iminobiotin is administered intravenous, intraarterial, intrathecal, subdural, subarachnoidal, subcapsular, subarachnoid, and/or intraspinal.

* * * * *